United States Patent
Ameer et al.

(10) Patent No.: US 10,463,769 B2
(45) Date of Patent: Nov. 5, 2019

(54) THROMBORESISTANT-ANTICOAGULANT EXTRACELLULAR MATRIX

(71) Applicant: Northwestern University, Evanston, IL (US)

(72) Inventors: Guillermo A. Ameer, Chicago, IL (US); Jason A. Wertheim, Evanston, IL (US); Bin Jiang, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/536,860

(22) PCT Filed: Dec. 18, 2015

(86) PCT No.: PCT/US2015/066729
§ 371 (c)(1),
(2) Date: Jun. 16, 2017

(87) PCT Pub. No.: WO2016/100846
PCT Pub. Date: Jun. 23, 2016

(65) Prior Publication Data
US 2017/0360992 A1     Dec. 21, 2017

Related U.S. Application Data

(60) Provisional application No. 62/094,724, filed on Dec. 19, 2014.

(51) Int. Cl.
*A61K 9/00*     (2006.01)
*A61L 27/54*    (2006.01)
(Continued)

(52) U.S. Cl.
CPC ............... *A61L 27/54* (2013.01); *A61L 27/20* (2013.01); *A61L 27/34* (2013.01);
(Continued)

(58) Field of Classification Search
CPC ...... A61L 27/18; A61L 27/3633; A61L 27/54; A61L 2300/236; A61L 2300/42;
(Continued)

(56) References Cited

U.S. PATENT DOCUMENTS 8,404,264 B2   3/2013 Ameer
8,568,765 B2  10/2013 Ameer et al.
(Continued)

OTHER PUBLICATIONS

Jiang et al. (Acta Biomaterialia 2015 (online Feb. 21, 2015);18:50-58). (Year: 2015).*
(Continued)

*Primary Examiner* — Ernst V Arnold
(74) *Attorney, Agent, or Firm* — Casimir Jones SC; David W. Staple

(57) ABSTRACT

Provided herein are bioactivated polymer/extracellular matrix (ECM) composites and methods of preparation and use thereof. In particular, heparinized cysteine-polymer/ECM composites, and methods of preparation and use thereof, are provided. In some embodiments, provided herein are compositions comprising a composite of: (a) extracellular matrix (ECM), and (b) a polyester covalently linked to a bioactive agent. In some embodiments, the composite is a homogeneous composite. In some embodiments, the ECM is decellularized ECM. In some embodiments, the ECM is not substantially crosslinked.

20 Claims, 23 Drawing Sheets

(51) Int. Cl.
| | |
|---|---|
| A61L 27/36 | (2006.01) |
| A61L 33/00 | (2006.01) |
| A61L 27/20 | (2006.01) |
| A61L 27/34 | (2006.01) |
| A61L 27/48 | (2006.01) |
| A61L 27/50 | (2006.01) |
| A61L 33/08 | (2006.01) |
| A61L 33/18 | (2006.01) |
| C08G 63/685 | (2006.01) |
| C08G 63/91 | (2006.01) |

(52) U.S. Cl.
CPC ........... *A61L 27/3633* (2013.01); *A61L 27/48* (2013.01); *A61L 27/507* (2013.01); *A61L 33/0011* (2013.01); *A61L 33/0088* (2013.01); *A61L 33/08* (2013.01); *A61L 33/18* (2013.01); *C08G 63/6854* (2013.01); *C08G 63/914* (2013.01); *A61L 2300/236* (2013.01); *A61L 2300/42* (2013.01)

(58) Field of Classification Search
CPC .......... A61L 27/20; A61L 27/34; A61L 27/48; A61L 27/507; A61L 33/0011; A61L 33/0088; A61L 33/08; A61L 33/18; C08L 67/04; C08L 77/04; C08G 63/6854; C08G 63/914
See application file for complete search history.

(56) References Cited

U.S. PATENT DOCUMENTS

| | | | |
|---|---|---|---|
| 8,580,912 B2 | 11/2013 | Ameer et al. | |
| 8,758,796 B2 | 6/2014 | Ameer et al. | |
| 8,772,437 B2 | 7/2014 | Ameer et al. | |
| 8,911,720 B2 | 12/2014 | Ameer et al. | |
| 2005/0013872 A1 | 1/2005 | Freyman | |
| 2007/0208420 A1* | 9/2007 | Ameer ................ | A61L 27/16 623/1.41 |
| 2011/0183435 A1* | 7/2011 | Yang .................. | A61L 27/18 436/501 |
| 2014/0037588 A1 | 2/2014 | Yang et al. | |
| 2014/0058049 A1 | 2/2014 | Ameer et al. | |
| 2014/0135407 A1 | 5/2014 | Ameer | |
| 2014/0155516 A1 | 6/2014 | Ameer et al. | |
| 2016/0129076 A1 | 5/2016 | Panitch et al. | |

OTHER PUBLICATIONS

Liao et al. (Biomaterials.2010; 31: 8911-8920). (Year: 2010).*
Hoshi et al. (Biomaterials. 2013;34:30-41). (Year: 2013).*
Zhang et al. (Biomaterials 2013;34(16):4048-4056). (Year: 2013).*
Albers et al., Meta-analysis of polytetrafluoroethylene bypass grafts to infrapopliteal arteries, J Vasc Surg, vol. 37(6), pp. 1263-1269, 2003.
Assmann et al., Development of a Growing Rat Model for the in Vivo Assessment of Engineered Aortic Conduits, J Surg Res, vol. 176(2), pp. 367-375, 2012.
Badylak et al., Extracellular matrix as a biological scaffold material: Structure and function, Acta Biomaterialia, vol. 5(1), pp. 1-13, 2009.
Badylak et al., Immune Response to Biologic Scaffold Materials, Semin Immunol, vol. 20(2), pp. 109-116, 2008.
Badylak, Xenogeneic extracellular matrix as a scaffold for tissue reconstruction, Transplant Immunology, vol. 12, pp. 367-377, 2004.
Bailey et al., Role of elastin in pathologic calcification of xenograft heart valves, J Biomed Mater Res Part a, vol. 66A(1), 2003.
Ballyk et al, Compliance mismatch may promote graft—artery intimal hyperplasia by altering suture-line stresses, Journal of Biomechanics, vol. 31(3), pp. 229-237, 1997.

Bergmeier et al., The role of platelet adhesion receptor GPIbαfar exceeds that of its main ligand, von Willebrand factor, in arterial thrombosis, PNAS, vol. 103(45), pp. 16900-16905, 2006.
Bergmeister et al., Decellularized, xenogeneic small-diameter arteries: Transition from a muscular to an elastic phenotype in vivo, J Biomed Mater Res Part B Appl Biomater, vol. 87B(1), p. 95, 2008.
Borschel et al., Tissue Engineering of Recellularized Small-Diameter Vascular Grafts, Tissue Eng, vol. 11, pp. 778-787, 2005.
Castellot et al., Inhibition of vascular smooth muscle cell growth by endothelial cell-derived heparin. Possible role of a platelet endoglycosidase, J Biol Chem, vol. 257(19), pp. 11256-11260, 1982.
Chang et al., In vivo evaluation of cellular and acellular bovine pericardia fixed with a naturally occurring crosslinking agent (genipin), Biomaterials, vol. 23(12), pp. 2447-2457, 2002.
Conklin et al., Development and evaluation of a novel decellularized vascular xenograft, Med Eng Phys, vol. 24(3), pp. 173-183, 2002.
Dahl et al., Decellularized Native and Engineered Arterial Scaffolds for Transplantation, Cell Transplantation, vol. 12(6), pp. 659-666, 2003.
Dahl et al., Readily Available Tissue-Engineered Vascular Grafts, Tissue Eng, vol. 3(68), pp. 68ra9, 2011.
Davie, A Brief Historical Review of the Waterfall/Cascade of Blood Coagulation, J Biol Chem, vol. 278(51), pp. 50819-50832, 2003.
Eitan et al., Acellular Cardiac Extracellular Matrix as a Scaffold for Tissue Engineering: In Vitro Cell Support, Remodeling, and Biocompatibility, Tissue Engineering Part C: Methods, vol. 16(4), pp. 671-683.
Ellman et al., A new and rapid colorimetric determination of acetylcholinesterase activity, Biochem Pharmacol, vol. 7(2), pp. 88-95, 1961.
Farndale et al., a Direct Spectrophotometric Microassay for Sulfated Glycosaminoglycans in Cartilage Cultures, Connective Tissue Research, vol. 9(4), pp. 247-248, 1982.
Fleisch et al., Inhibition of Aortic Calcification by means of Pyrophosphate and Polyphosphates, Nature, vol. 207, pp. 1300-1301, 1965.
Greenwald et al., Improving vascular grafts: the importance of mechanical and haemodynamic properties, J Pathol, vol. 190, pp. 292-299, 2000.
Griese et al., Isolation and Transplantation of Autologous Circulating Endothelial Cells Into Denuded Vessels and Prosthetic Grafts: Implications for Cell-Based Vascular Therapy, Circulation, vol. 108, pp. 2710-2715, 2003.
Haraguchi et al., Intimal hyperplasia and hemodynamic factors in arterial bypass and arteriovenous grafts: a review, Artificial Organs, vol. 6(4), pp. 227-235, 2003.
Hirsh et al., Heparin and Low-Molecular-Weight Heparin: the Seventh Accp Conference on Antithrombotic and Thrombolytic Therapy, Chest, vol. 126(3), pp. 188S-203S, 2004.
Iredale, Models of liver fibrosis: exploring the dynamic nature of inflammation and repair in a solid organ, J Clin Invest, vol. 117(3), pp. 539-548, 2007.
Jiang et al., a polymer-extracellular matrix composite with improved thromboresistance and recellularization properties, Acta Biomaterialia, vol. 18, pp. 50-58, 2015.
Jiang et al., Enabling Non-invasive Assessment of an Engineered Endothelium on ePTFE Vascular Grafts without Increasing Oxidative Stress, Biomaterials, vol. 69, pp. 110-120, 2015.
Johnson et al., Vascular Calcification: Pathobiological Mechanisms and Clinical Implications, Circ Res, vol. 99, pp. 1044-1059, 2006.
Kaushal et al., Functional Small Diameter Neovessels using Endothelial Progenitor Cells Expanded Ex Vivo, Nat Med, vol. 7(9), pp. 1035-1040, 2001.
Lemson et al., Intimal Hyperplasia in Vascular Grafts, Eur J Vasc Endovasc Surg, vol. 19, pp. 336-350, 2000.
Leventhal et al., Matrix Crosslinking Forces Tumor Progression by Enhancing Integrin Signaling, Cell, vol. 139(5), pp. 891-906, 2009.
Liao et al., Bioactive polymer/extracellular matrix scaffolds fabricated with a flow perfusion bioreactor for cartilage tissue engineering, Biomaterials, vol. 31(34), pp. 8911-8920, 2010.

(56) References Cited

OTHER PUBLICATIONS

Majack et al., Inhibition of vascular smooth muscle cell migration by heparin-like glycosaminoglycans, J Cell Physiol, vol. 118(3), 1984.

Maldonado et al., the Role of Changes in Extracellular Matrix of Cartilage in the Presence of Inflammation on the Pathology of Osteoarthritis, BioMed Research International, vol. 2013, article Id 284873, 10 pp., 2013.

Melchiorri et al., Strategies and Techniques to Enhance the in Situ Endothelialization of Small-Diameter Biodegradable Polymeric Vascular Grafts, Tissue Eng Part B Rev, vol. 19(4), pp. 292-307, 2013.

Murugesan et al., Immobilization of Heparin: Approaches and Applications, Curr Top Med Chem, vol. 8(2), pp. 80-100, 2008.

Nair et al., Efficacy of solvent extraction methods for acellularization of embryoid bodies, vol. 19(6), pp. 801-819, 2012.

Newby et al., Molecular mechanisms in intimal hyperplasia, J Pathol, vol. 190(3), pp. 300-309, 2000.

Ngangan et al., Acellularization of embryoid bodies via physical disruption methods, Biomaterials, vol. 30(6), pp. 1143-1149, 2009.

Park et al., Characterization of porous collagen/hyaluronic acid scaffold modified by 1-ethyl-3-(3-dimethylaminopropyl)carbodiimide cross-linking, Biomaterials, vol. 23(4), pp. 1205-1212, 2002.

Park et al., Role of Inflammation in the Pathogenesis of Arterial Stiffness, Yonsei Med J, vol. 53(2), pp. 258-261, 2012.

Pektok et al., Degradation and Healing Characteristics of Small-Diameter Poly( - Caprolactone) Vascular Grafts in the Rat Systemic Arterial Circulation, Circulation, vol. 118, pp. 2563-2570, 2008.

Pilipchuk et al., Influence of crosslinking on the stiffness and degradation of dermis-derived hydrogels, J Biomed Res Part a, vol. 101(10), 2013.

Quint et al., Allogeneic human tissue-engineered blood vessel, J Vasc Surg, vol. 55(3), pp. 790-798, 2012.

Reing et al., Degradation Products of Extracellular Matrix Affect Cell Migration and Proliferation, Tissue Engineering, vol. 15(3), pp. 605-614, 2009.

Reynolds et al., Multifunctional Roles for Serum Protein Fetuin-A in Inhibition of Human Vascular Smooth Muscle Cell Calcification, Jasn, vol. 16(10), pp. 29202930, 2005.

Sarkar et al., the Mechanical Properties of Infrainguinal Vascular Bypass Grafts: Their Role in Influencing Patency, Eur J Vasc Endovasc Surg, vol. 31(6), pp. 627-636, 2006.

Schmidt et al., Acellular vascular tissues: natural biomaterials for tissue repair and tissue engineering, Biomaterials, vol. 21(22), pp. 2215-2231, 2000.

Schurgers et al., Matrix Gla-protein: the calcification inhibitor in need of vitamin K, Thromb Haemost, vol. 100(4), pp. 593-603, 2008.

Serrano et al., Novel Biodegradable Shape-Memory Elastomers with Drug-Releasing Capabilities, Adv Mater, vol. 23(19), pp. 2211-2215, 2011.

Shao et al., Inflammation and the Osteogenic Regulation of Vascular Calcification: a Review & Perspective, Hypertension, vol. 55(3), pp. 579-592, 2010.

Shimizu et al., Host bone-marrow cells are a source of donor intimal smooth-muscle-like cells in murine aortic transplant arteriopathy, Nat Med, vol. 7, pp. 738741, 2001.

Steinhoff et al., Tissue Engineering of Pulmonary Heart Valves on Allogenic Acellular Matrix Conduits, Circulation, suppl. III, pp. III50-III55, 2000.

Tischer et al., Tissue engineering of the anterior cruciate ligament: a new method using acellularized tendon allografts and autologous fibroblasts, Arch Orthop Trauma Surg, vol. 127(9), pp. 735-741, 2007.

Van Lith et al., Engineering biodegradable polyester elastomers with antioxidant properties to attenuate oxidative stress in tissues, Biomaterials, vol. 35(28), pp. 8113-8122, 2014.

Wong et al., Endothelial Cells Derived From Nuclear Reprogramming, Circ Res, vol. 111(10), pp. 1363-1375, 2012.

Yang et al., a Thermoresponsive Biodegradable Polymer with Intrinsic Antioxidant Properties, Biomacromolecules, vol. 15(11), pp. 3942-3952, 2014.

Yang et al., Development of aliphatic biodegradable photoluminescent polymers, Pnas, vol. 106(25), pp. 10086-10091, 2009.

Yang et al., Modulating Expanded Polytetrafluoroethylene Vascular Graft Host Response via Citric Acid-Based Biodegradable Elastomers, Adv Mater, vol. 18(12), pp. 1493-1498, 2006.

Yang et al., Synthesis and evaluation of poly(diol citrate) biodegradable elastomers, Biomaterials, vol. 27(9), pp. 1889-1898, 2006.

Zhou et al., Development and Validation of Small-diameter Vascular Tissue From a Decellularized Scaffold Coated With Heparin and Vascular Endothelial Growth Factor, Artificial Organs, vol. 33(3), pp. 230-239, 2009.

International Search Report of related PCT/US2015/066729, mailed Apr. 22 2016, 15 pages.

\* cited by examiner

THROMBORESISTANT-ANTICOAGULANT EXTRACELLULAR MATRIX

CROSS-REFERENCE TO RELATED APPLICATIONS

The present invention claims the priority benefit of U.S. Provisional Patent Application 62/094,724, filed Dec. 19, 2014, which is incorporated herein by reference in its entirety.

FIELD

Provided herein are bioactivated polymer/extracellular matrix (ECM) composites and methods of preparation and use thereof. In particular, heparinized cysteine-polymer/ECM composites, and methods of preparation and use thereof, are provided.

BACKGROUND

Small vessel thrombosis is one of the major hurdles when using decellularized extracellular matrix (ECM) as a tissue/organ engineering scaffold. Heparin is often immobilized onto the ECM to provide anticoagulant activity. However, strategies to immobilize heparin onto ECM involve chemical crosslinking, which increases the mechanical stiffness and alters the ultrastructure of the ECM. It is important for the ECM to maintain its native mechanical properties and structure for its proper function.

SUMMARY

Provided herein are bioactivated polymer/extracellular matrix (ECM) composites and methods of preparation and use thereof. In particular, heparinized cysteine-polymer/ECM composites, and methods of preparation and use thereof, are provided.

In some embodiments, provided herein are compositions comprising a composite of: (a) extracellular matrix (ECM), and (b) a polyester covalently linked to a bioactive agent. In some embodiments, the composite is a homogeneous composite. In some embodiments, the ECM is decellularized ECM. In some embodiments, the ECM is not substantially crosslinked. In some embodiments, the ECM is not crosslinked substantially more than naturally-occurring ECM in vivo. In some embodiments, the polyester comprises citric acid monomers. In some embodiments, the polyester comprises aliphatic diol monomers. In some embodiments, the aliphatic diol monomers are 4-16 carbons (e.g., 4, 5, 6, 7, 8, 9, 10, 11, 12, 13, 14, 15, 16, or ranges there between) in length. In some embodiments, the diol have terminal OH groups (e.g., at the 1 and 10 carbons of a 10 carbon diol (e.g., decanediol)). In some embodiments, the aliphatic diol monomers comprise 1,8-octandiol. In some embodiments, the polyester comprises cysteine monomers. In some embodiments, the bioactive agent is covalently linked to the polyester at one or more of the cysteine monomers. In some embodiments, the bioactive agent is selected from an anticoagulant, growth factor, cytokine, and hormone. In some embodiments, the bioactive agent is heparin.

In some embodiments, provided herein is a composition comprising a composite of: (a) ECM; and (b) a polyester co-cysteine, wherein the polyester co-cysteine is covalently linked to a bioactive agent via a thiolate linkage at a cysteine monomer. In some embodiments, the polyester co-cysteine is poly(diol citrate) co-cysteine. In some embodiments, the polyester co-cysteine is poly(1,8-octanediol citrate) co-cysteine. In some embodiments, the bioactive agent is selected from an anticoagulant, growth factor, cytokine, and hormone. In some embodiments, the bioactive agent is heparin. In some embodiments, the composite is a homogeneous composite. In some embodiments, the ECM is decellularized ECM. In some embodiments, the ECM is not substantially crosslinked. In some embodiments, the ECM is not crosslinked substantially more than naturally-occurring ECM in vivo. In some embodiments, any degree of crosslinking present in the ECM is naturally-occurring and/or does not impact the structure and/or physical characteristics of the ECM.

In some embodiments, provided herein are compositions comprising a composite of: (a) extracellular matrix (ECM), and (b) a citric acid polyester. In some embodiments, the citric acid polyester comprises aliphatic diol monomers. In some embodiments, the aliphatic diol monomers are 4-16 carbons (e.g., 4, 5, 6, 7, 8, 9, 10, 11, 12, 13, 14, 15, 16, or ranges there between) in length. In some embodiments, the diol have terminal OH groups (e.g., at the 1 and 10 carbons of a 10 carbon diol (e.g., decanediol)). In some embodiments, the aliphatic diol monomers comprise 1,8-octandiol. In some embodiments, the citric acid polyester comprises cysteine monomers. In some embodiments, the citric acid is a poly(diol citrate) co-cysteine. In some embodiments, the citric acid polyester co-cysteine is poly(1,8-octanediol citrate) co-cysteine (POC-cys).

In some embodiments, provided herein are methods of immobilizing a bioactive agent within extracellular matrix (ECM), comprising reacting a first clicking group on the bioactive agent with a complementary clicking group on a polymer, the polymer being in a composite with the ECM, thereby immobilizing the bioactive agent on the polymer. In some embodiments, methods further comprise a prior step of reacting the bioactive agent with a molecular entity comprising the first clicking agent. In some embodiments, methods further comprise a prior step of contacting the ECM with a pre-polymer and allowing the pre-polymer to further polymerize within the ECM to form the composite. In some embodiments, methods further comprise a prior step of forming a pre-polymer comprising a monomer until displaying the complementary clicking group. In some embodiments, the ECM is decellularized ECM. In some embodiments, the ECM is not substantially crosslinked. In some embodiments, the ECM is not crosslinked substantially more than naturally-occurring ECM in vivo. In some embodiments, the polymer comprises a polyester. In some embodiments, the polyester comprises citric acid monomers. In some embodiments, the polyester comprises aliphatic diol monomers. In some embodiments, the aliphatic diol monomers are 4-16 carbons (e.g., 4, 5, 6, 7, 8, 9, 10, 11, 12, 13, 14, 15, 16, or ranges there between) in length. In some embodiments, the diol have terminal OH groups (e.g., at the 1 and 10 carbons of a 10 carbon diol (e.g., decanediol)). In some embodiments, the aliphatic diol monomers comprise 1,8-octandiol. In some embodiments, the polyester comprises cysteine monomers. In some embodiments, the bioactive agent is covalently linked to the polyester at one or more of the cysteine monomers. In some embodiments, the bioactive agent is selected from an anticoagulant, growth factor, cytokine, and hormone. In some embodiments, the bioactive agent is heparin.

In some embodiments, provided herein are methods of tissue repair or engineering, comprising implanting a bioactivated (e.g., heparinized) polymer/ECM composite described herein into a subject.

Use of a bioactivated (e.g., heparinized) polymer/ECM composite described herein for tissue repair or engineering.

DEFINITIONS

Figure 1:
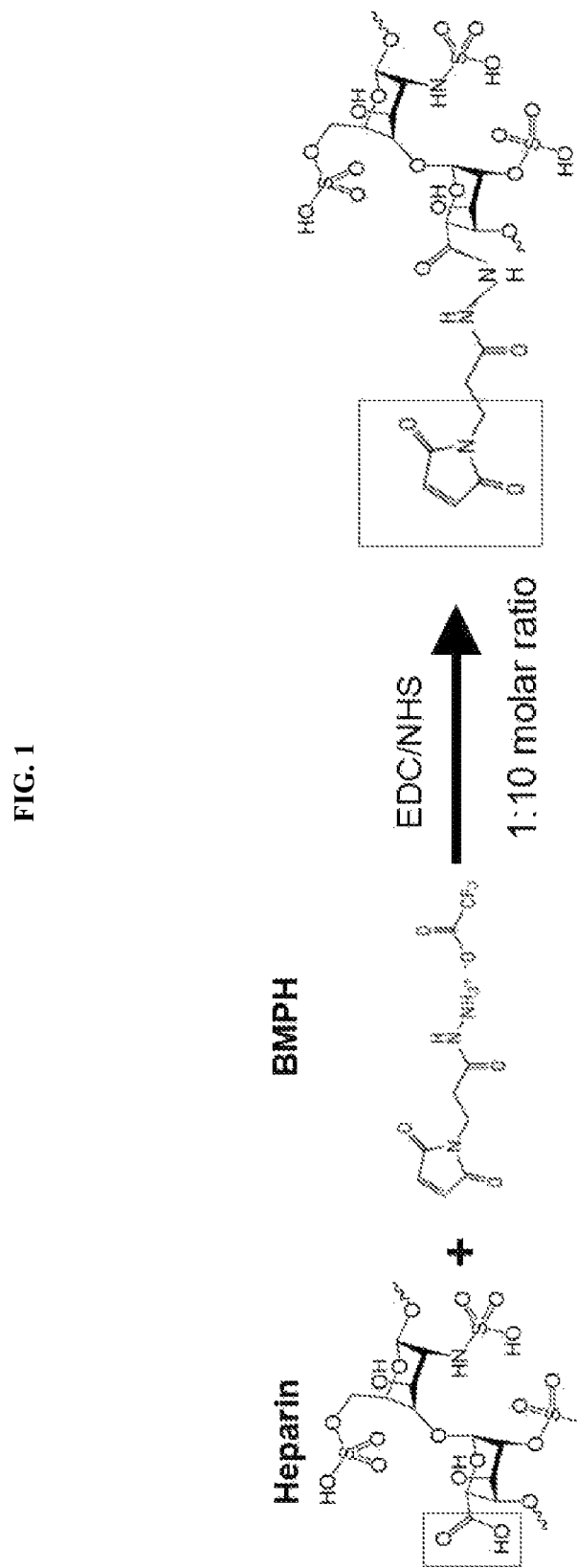
FIG. 1 shows a schematic representation of Heparin-BMPH conjugation process.

As used herein, the term "extracellular matrix", abbreviated "ECM", refers to the complex structural material produced by cells in mammalian tissues (e.g., particularly cells of connective tissue, for instance such cells as fibroblasts, osteoblasts, chondrocytes, epithelial cells, smooth muscle cells, adipocytes, mesenchymal cells, etc.) which surrounds and supports the cells in vivo. Typically, the ECM is composed of fibers embedded in what is commonly referred to as 'ground substance.' ECM include proteins in the fibers as structural proteins ("ECM fibers" or "ECM fiber proteins"), such as collagen and/or elastin. Particularly suitable collagens are fibril-forming collagens, such as type I collagen, type II collagen, type III collagen, type IV collagen or type X collagen. ECM also includes proteins in the 'ground substance' of ECM ("ECM ground" or "ECM ground proteins"). Additional ECM proteins may include, for example, glycoproteins, such as laminin, entactin, tenascin, fibrillin, or fibronectin, for improving structural integrity of the network and for the attachment of cells to the ECM; osteocalcin (Gla protein), as a protein that binds calcium during mineralization; osteonectin, which serves a bridging function between collagen and mineral component; and sialoproteins, such as bone sialoprotein (BSP), osteopontin (OPN), dentin matrix protein-1 (DMP1), dentin sialophosphoprotein (DSPP) and matrix extracellular phosphoglycoprotein (MEPE). ECM refers both to the material in vivo, as well as to the material in isolated form, separated from the cells that produced it ("decellularized ECM" ("dECM"))). The formation of covalent linkages between carboxyl and amine groups within the ECM results in "crosslinked ECM" ("cECM").

As used herein, the term "polymer" refers to a chain of repeating structural units (e.g., citric acid, aliphatic diol, amino acids (e.g., cysteine), etc.) or "monomers", typically of large molecular mass. Examples of polymers include homopolymers (single type of monomer subunits), copolymers (two types of monomer subunits), and heteropolymers (e.g., three or more types of monomer subunits). As used herein, the term "oligomer" refers to a polymer of only a few monomer units (e.g., 2, 3, 4, 5, or more) up to about 50 monomer units, for example a dimer, trimer, tetramer, pentamer, hexamer . . . decamer, etc.

As used herein, the term "linear polymer" refers to a polymer in which the molecules form long chains without branches or crosslinked structures.

As used herein, the term "branched polymer" refers to a polymer comprising a polymer backbone with one or more additional monomers, or chains or monomers, extending from polymer backbone. The degree of interconnectedness of the "branches" is insufficient to render the polymer insoluble.

As used herein, the terms "pre-polymer" and "pre-oligomer" refer to linear or branched polymers and oligomers (e.g., not significantly crosslinked, soluble) that have the capacity to be crosslinked under appropriate conditions, but which have not yet been subjected to the appropriate conditions.

As used herein, the term "crosslinked polymer" refers to a polymer with a significant degree of interconnectedness between multiple polymer strands, the result of which is an insoluble polymer network. For example, multiple polymer stands may be crosslinked to each other at points within their structures, not limited to the ends of the polymer chains.

As used herein, the term "composite" refers to a material comprising two or more molecular, polymeric, and/or supramolecular constituents that are miscible with one another, and may form a single homogeneous material. While covalent connections between the constituent components may be present, they are not required to form or maintain the composite or its homogeneity; rather, non-covalent and/or mechanical/physical interactions and associations are responsible for stabilizing the composite.

As used herein, the term "click chemistry" refers to the use of chemical building blocks ("clicking groups") with built-in high-energy content to drive a spontaneous and irreversible linkage reaction with appropriate complementary sites in other blocks. These chemical reactions (e.g., including, but not limited to, those between maleimide and thiol groups that combine readily with each other) are specific and result in covalent linkage between the two blocks or clicking groups. Suitable clickable/clicking pairs include thiol/maleimide, azide/alkyne and thiol/alkene.

As used herein, the term "bioactive agent," refers to a molecular entity which exerts a physiological, therapeutic or diagnostic effect in vivo. Bioactive agents may be organic or inorganic. Representative examples include proteins, peptides, carbohydrates, lipids, nucleic acids, polymers/oligomers, anti-viral compounds, anti-inflammatory compounds, antibiotic compounds such as antifungal and antibacterial compounds, cell differentiating agents, analgesics, contrast agents for medical diagnostic imaging, enzymes, cytokines, anaesthetics, antihistamines, anticoagulants (e.g., heparin), agents that act on the immune system, hemostatic agents, hormones, angiogenic or anti-angiogenic agents, neurotransmitters, therapeutic oligonucleotides, viral particles, vectors, growth factors, retinoids, cell adhesion factors, osteogenic factors, antibodies and antigens, steroids, painkillers.

As used herein, the term "bioactivated" refers to a compound, polymer, or other material that has been modified to display a bioactive agent or moiety. The term "bioactivated" may be used herein synonymously with the term "functionalized."

The term "heparinized" refers herein to a molecular entity (e.g., compound, polymer, composite) to which heparin (e.g., unfractionated heparin, fractionated heparin, low-molecular-weight heparin, etc.) has been covalently bound.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-akylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "substantially all," "substantially complete" and similar terms refer to greater than 99%; and the terms "substantially none," "substantially free of" and similar terms refer to less than 1%.

The term "about" allows for a degree of variability in a value or range. As used herein, the term "about" refers to values within 10% of the recited value or range (e.g., about 50 is the equivalent of 45-55).

DETAILED DESCRIPTION

Provided herein are bioactivated polymer/extracellular matrix (ECM) composites and methods of preparation and use thereof. In particular, heparinized cysteine-polymer/ECM composites, and methods of preparation and use thereof, are provided.

I. General

In some embodiments, a bioactive agent displaying a first clicking group is reacted with a composite of ECM and a polymer displaying a second clicking group, the first and second clicking groups being selectively reactive with one another, so as to produce a covalent linkage between the bioactive agent and the polymer of the polymer/EMC composite, yielding a bioactivated polymer/ECM composite.

In some embodiments, provided herein are polymers and pre-polymers comprising a cysteine monomer, a modified-cysteine monomer, or other thiol-presenting monomer (e.g., among other monomers present in the polymer/prepolymer). In some embodiments, composites of a thiol-presenting polymer or pre-polymer and extracellular matrix (e.g., decellularized ECM) are provided (e.g., under conditions suitable from polymerization (or crosslinking) of the pre-polymer (but not the ECM) to form a composite of the polymer and the ECM). In some embodiments, composites of a thiol-presenting polymer and ECM (e.g., decellularized ECM) are provided. In some embodiments, a bioactive agent (e.g., heparin, a growth factor, a cytokine, etc.) displaying a thiol-reactive clicking group (e.g., alkene, maleimide, alkyne, etc.) is provided. In some embodiments, a bioactive agent displaying a thiol-reactive clicking group is reacted with a composite of a thiol-presenting polymer and ECM to yield a bioactivated polymer/ECM composite.

In some embodiments, provided herein are methods of heparin (or another bioactive agent (e.g., growth factor, cytokine, pharmaceutical, etc.)) immobilization onto/within ECM via click chemistry (e.g., maleimide-thiol chemistry) between clicking groups on the heparin and a polymer (e.g., thiol-presenting polymer (e.g., cysteine-containing polymer (e.g., citric acid/cysteine polymer (e.g., poly(diol citric acid)-co-cysteine (e.g., POC-Cys, etc.), etc.), etc.), etc.) that is part of a composite with the ECM.

Embodiments herein use a polymer component of a composite with the ECM for attachment of the bioactive agent (e.g., heparin). Some embodiments herein use a co-polymer POC-Cys for attachment of the thiol-reactive bioactive agent (e.g., heparin-BMPH), which is much easier and cheaper to produce, and offers more control over the amount of —SH groups than using peptide.

During experiments conducted leading to development of embodiments herein, ECM (decellularized rat aortas) was heparinized by crosslinking carboxyl and primary amine groups within the ECM (e.g., via carbodiimide chemistry (e.g., 1-ethyl-3-(-3-dimethylaminopropyl) carbodiimide hydrochloride (EDC)), thereby containing the heparin within the crosslinked ECM (cECM). However, the crosslinking increased the stiffness of the ECM and caused severe intimal hyperplasia when implanted. In light of the above, the systems and methods herein were developed to immobilize heparin within ECM without crosslinking of the ECM, and while maintaining the physical characteristics of ECM. In some embodiments, provided herein are methods for heparin immobilization within ECM (e.g., to the ECM directly or to a polymer composite with the ECM), and compositions resulting therefrom. In some embodiments, methods herein employ: (1) conjugating heparin with (N-[ε-maleimidopropionic acid] hydrazide) (BMPH) as a linker via standard carbodiimide chemistry; (2) freeing thiols within the ECM via a reducing agent and/or coating the ECM with poly(1,8-octanediol citric acid)-co-cysteine (POC-Cys); (3) reacting heparin-BMPH with the SH-ECM or the POC-Cys-coated ECM, to allow covalent bonds formation between thiols of the ECM or POC-Cys and maleimides of BMPH, thus linking heparin onto the ECM.

In some embodiments, provided herein are methods to immobilize heparin onto ECM, for example, via polymer-ECM hybridization followed by maleimide-thiol "click" chemistry. These methods allow the immobilization of active heparin molecules onto ECM without crosslinking, therefore improving ECM thromboresistant properties while maintaining natural ECM mechanical properties. Evaluated in a rodent aorta interposition model, mechanocompatible heparinized polymer-ECM composite grafts decreased intimal hyperplasia formation in the midgraft and did not increase inflammation, which is in direct contrast to polymer-cECM grafts. Findings indicate that mechanocompatible heparinized polymer-ECM composites are superior to traditional crosslinking chemistry (e.g., to produce cECM), and maintain native ECM properties and bioactive function.

In some embodiments, methods are provided for the immobilizing bioactive agents (e.g., heparin, growth factors (e.g., vascular endothelial growth factor (VEGF), bone morphogenic proteins (e.g., BMP-2), transforming growth factor beta, etc.), cytokines, growth factor binding peptides, etc.) onto ECM (e.g., for tissue engineering applications) without crosslinking of the ECM. Using maleimide-thiol "click" chemistry to functionalize polymer-ECM composites provides a platform useful to link other bioactive molecules onto ECM based scaffolds without ECM crosslinking for various tissue engineering applications. In some embodiments, growth factors or cytokines such as vascular endothelial growth factor (VEGF) are modified with BMPH and linked to POC-Cys coated arterial ECM to improve EC recruitment and enhance endothelialization of vascular grafts. In some embodiments, to prevent calcification of acellular vascular grafts and heart valves, calcification inhibitors such as MGP are immobilized onto the polymer-ECM composite scaffolds using "click" chemistry, without chemical crosslinking. In some embodiments, methods and systems herein are applied to regenerative medicine, where the fate of stem cells seeded onto tissue-specific ECM scaffold are controlled by spatially presenting various signaling proteins on tissue-specific ECM. In some embodiments, a similar strategy is applied to whole organ engineering to modify the ECM of intraparenchymal vessels in organs such as the heart, kidney and liver, to enhance thromboresistance and recellularization without altering mechanical properties.

II. Polymer

In some embodiments, compositions and composites described herein comprise a polymeric component (e.g., the polymer component of a polymer/ECM composite). In some embodiments, the polymeric component comprises a chain of monomer constituents, either (a) including a monomer displaying a clicking group; or (b) a monomer with (i) a clicking group or (ii) a moiety comprising a clicking group, appended thereto.

In some embodiments, the polymer comprises a monomer displaying a clicking group selected from those described herein or known in the art, such as a thiol, azide, alkene, alkyne, maleimide, transcyclooctene, tetrazine, dibenzocyclooctyne, etc. In some embodiments, the monomer comprises the clicking group (e.g., a cysteine comprises a thiol). In other embodiments, a monomer within a polymer comprises a group to which a clicking group or agent comprising a clicking group (e.g., BMPH) is appended.

In some embodiments, a monomer comprising a clicking group is included in the synthesis of a polymer comprising other monomeric subunits. In some embodiments, the polymer within which the monomer displaying the clicking group is included (or a clicking group or moiety is appended) is selected from a polyester, poly(diol citrate) (e.g., poly(butanediol citrate), poly(hexanediol citrate), poly(octanediol citrate), poly(decanediol citrate), poly(dodecanediol citrate), poly(hexadecanediol citrate), etc.), poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, or co-polymers or composites thereof.

In some embodiments, a polymer component comprises a citric acid-based polymer. In some embodiments, a polymer is the polyesterification product of one or more acids (e.g., succinic acid, glutaric acid, adipic acid, pimelic acid, suberic acid, azelaic acid, sebacic acid, dodecanedioic acid, shorter or longer linear aliphatic diacids, citric acid, isocitric acid, aconitic acid, propane-1,2,3-tricarboxylic acid, trimesic acid, itaconic acid, maleic acid, etc.) and one or more diols or triols (e.g., polyethylene glycol, glycerol, linear aliphatic diol (e.g., butanediol, hexanediol, octanediol, decanediol, dodecanediol, and shorter or longer linear aliphatic diols), etc.). In some embodiments, a polymer is the polyesterification product of an acid, a diol or triol, and a monomer comprising or displaying a clicking group (e.g., cysteine (displaying a thiol)).

In some embodiments, a polymer is the polyesterification product of at least citric acid, one or more linear aliphatic diols (butanediol, hexanediol, octanediol, decanediol, dodecanediol, or any linear aliphatic diol from about 2-20 carbons in length), and a monomer displaying a clicking group (e.g., cysteine). A polymer may further comprise additional monomer components (e.g., sebacic acid, polyethylene glycol, glycerol, etc.). In some embodiments, a polymer comprises additional substituents or functional groups appended to the polymer (e.g., ascorbic acid, glycerol, etc.).

In some embodiments, polymeric components comprise citric acid as a monomer (e.g., along with a diol monomer). Citric acid is a reactive tricarboxylic acid that is part of the Krebs cycle and has been used as a key reactant monomer for the synthesis of polydiolcitrates with a wide range of properties and uses (Yang, J., et al., Synthesis and evaluation of poly(diol citrate) biodegradable elastomers. Biomaterials, 2006. 27(9): p. 1889-98; U.S. Pat. Nos. 8,772,437; 8,758,796; 8,580,912; 8,568,765; U.S. Pub. No. 2014/0155516; U.S. Pub. No. 2014/0135407; herein incorporated by reference in their entireties). Depending on the diol of choice, materials with controllable elasticity, biodegradability, and antioxidant properties can be developed (Serrano et al. Adv Mater, 2011. 23(19): p. 2211-5; Yang J., et al., A thermoresponsive biodegradable polymer with intrinsic antioxidant properties. Biomacromolecules, 2014. 15(11):3942-52; U.S. Pub. No. 2014/0037588; herein incorporated by reference in its entirety).

In some embodiments, reagents, monomer components of polymers, methods, reaction conditions, etc. that find use in embodiments described herein are described in: U.S. Pat. Nos. 8,911,720; 8,772,437; 8,758,796; 8,580,912; 8,568,765; 8,404,264; U.S. Pub. No. 2014/0058049; U.S. Pub. No. 2013/0211500; herein incorporated by reference in their entireties.

In some embodiments, the polymer component of the composite is a polymer comprising cysteine monomers. In some embodiments, the polymer comprises an acid monomer and a cysteine monomer. In some embodiments, the polymer comprises citric acid and cysteine monomers. In some embodiments, the polymer comprises acid, diol or triol, and cysteine monomers. In some embodiments, the polymer comprises citric acid, diol, and cysteine monomers. In some embodiments, the polymer comprises poly (diol citrate) co-cysteine. In some embodiments, the polemer comprises poly(butanediol citrate) co-cysteine, poly (hexanediol citrate) co-cysteine, poly(octanediol citrate) co-cysteine, poly(decanediol citrate) co-cysteine, poly(dodecanediol citrate) co-cysteine, poly(hexadecanediol citrate) co-cysteine, etc.

III. ECM

Extracellular matrix (ECM) is a secreted product of cells that populate in a given tissue or organ. The ECM influences the behavior and phenotype of the resident cells. Cell attachment, migration, proliferation and three-dimensional arrangement are strongly affected by matrix composition and structure. Advantages of using ECM scaffolds in bioengineering and tissue repair applications include their bioactivity and biocompatibility capabilities.

ECM compositions typically include the most abundant protein-type I Collagen, as well as fibronectin and laminin. Other substantial components are glycosaminoglycans, as chrondrotin sulfate, heparin and hyaluronic acid, which have superior binding properties of bioactive molecules as growth factors and cytokines. Growth factors, such as vascular endothelial growth factor (VEGF), fibroblast growth factor (FGF), epidermal growth factor (EGF), and TGF-, are present within the ECM in very small quantities but typically play roles as potent modulators of cell behavior.

ECMs for clinical applications are derived from organs such as the small intestine, urinary bladder or skin (Reing J., et al. 2009, Tissue Engineering, Vol. 15: 605-614; Badylak S F. 2004. Transplant Immunology 12: 367-377; herein incorporated by reference in their entireties), from allogeneic (human cadavers) or xenogeneic sources (porcine, bovine or equine small intestine submucosa, dermis and pericardium). Both cellular and acellular forms of ECM scaffolds have been used for tissue engineering applications.

In some embodiments, ECM used in embodiments herein includes fibrous elements (e.g., collagen, elastin, or reticulin), cell adhesion polypeptides (e.g., fibronectin, laminin and adhesive glycoproteins), and space-filling molecules (e.g., glycosaminoglycans (GAG), proteoglycans, etc.).

The term "isolated" as used herein in reference to ECM refers to at least partial separation from the natural environment (e.g., the cells producing the ECM). Decullularization is a form of isolation.

According to some embodiments, the ECM comprises proteins such as collagens (e.g., various types as collagen I, collagen III, IV, V, VI), actin, Vimentin, fibronectin and laminin, desmin, Glucoseaminoglycans (GAGs).

In some embodiments, the ECM is a non-mineralized ECM. As used herein the phrase "non-mineralized" ECM refers to an ECM which is substantially devoid of calcium deposits. According to some embodiments, the ECM comprises no more than 10% (weight/weight) of calcium deposits, e.g., no more than about 9%, nor more than about 8%, 7%, 6%, 5%, 4%, 3%, 2%, 1% of calcium, e.g., 0% calcium deposits.

In some embodiments, in order to be amendable for tissue regeneration or repair applications, the ECM is devoid of cellular components. In some embodiments, methods comprise decellularizing the extracellular matrix. As used herein the phrase "decellularizing the ECM" refers to removal of cells from the ECM. According to some embodiments, the isolated ECM is decellularized. According to some embodiments, the isolated ECM is devoid of any cellular components (e.g., acellular ECM). The phrase "devoid of any cellular components" as used herein refers to being more than about 80%, e.g., more than 81%, 82%, 83%, 84%, 85%, 86%, 87%, 88%, 89%, 90%, 91%, 92%, 93%, 93%, 94%, 95%, 96%, 97%, 98%, 99%, e.g., 100% devoid of the cellular components present in the cell culture which comprises the ECM prior to the decellularization process. As used herein, the phrase "cellular components" refers to cell membrane components or intracellular components which make up the cell. Examples of cell components include cell structures (e.g., organelles) or molecules comprised in same. Examples of such include, but are not limited to, cell nuclei, nucleic acids, residual nucleic acids (e.g., fragmented nucleic acid sequences), cell membranes and/or residual cell membranes (e.g., fragmented membranes) which are present in cells of the tissue.

Decellularization of the ECM may be performed by various methods known in the art. For example, acellularization can be performed by combination of physical treatment-lyophilization, freeze and thaw cycling and DNase treatment, essentially as described in Ngangan A V and McDevitt T C (2009, Biomaterials 30:1143-1149 which is fully incorporated herein by reference in its entirety); acellularization may be performed by Peracetic acid, Sodium dodecyl sulfate, Tritonx100 and DNase essentially as described in Nair R. et al. (2008, J. Biomater. Sci. Polymer Edn. 19: 801-819, which is fully incorporated herein by reference in its entirety); acellularization may be performed by treatment with distilled water (e.g., Aqua dest) for 24 hours, 1% SDS for 24 hours, distilled water for 24 hours and 70% Ethanol for 24 hours, followed by washes with PBS, essentially as described in Tischer T. et al. (2007, Arch Orthop Trauma Surg. 127:735-741, which is fully incorporated herein by reference in its entirety); acellularization m be performed by washes in hypertonic 1.1% NaCl-0.02% ethylenediaminetetraacetic acid (EDTA; Sigma, St. Louis, Mo.) for 2 hours and then in hypotonic 0.7% NaCl-0.02% EDTA for 2 hours, followed by two 24 hours cycles of enzymatic digestion using 0.05% trypsin (Sigma)-0.02% EDTA in PBS at pH 7.4 and at 37° C., supplemented with Pen-Strep and Fungizone, followed by wash(es) in detergent solution of 1% Triton-X-100 (polyethylene octylphenyl ether) and 0.1% ammonium hydroxide in PBS for four consecutive 48 hours cycles, and extensive washes in sterile saline, immersion in 70% ethanol overnight, and washes in sterile water, and lyophilization, essentially as described in Eitan Y. et al. (2010, Tissue engineering part C Methods. 16(4):671-83; which is fully incorporated herein by reference in its entirety); acellularization can be performed by combination of physical and chemical treatments as—sonication, agitation, freezing and thawing, and then several detergent washes, essentially as described in Badylak S F et al. 2009 (ActaBiomaterialia, 5: 1-13, which is fully incorporated herein by reference in its entirety).

In some embodiments, by whatever method the ECM is decellularized, the decellularization process is performed such that the cellular components are removed while the ECM is sunbstantially unharmed, and exhibits the same structural and mechanical properties as the ECM prior to the decellularization process.

In some embodiments, any processes to which the ECM is subjected to (e.g., decellularization, polymerization of monomers or pre-polymer, etc.) do not result in significant crosslinking of the ECM (e.g., little or no carboxyl to amine attachment within the ECM).

In previous attempts to use ECM for tissue repair or regeneration, ECM is crosslinked between the amines and carboxyls therein (e.g., producing cECM). Various methods of such crosslinking are understood in the art. In some embodiments herein, polymer/ECM compositesd are bioactivated without crosslinking, or without substantial crosslinking, or without non-natural amounts of crosslinking of the ECM.

IV. Composite

In some embodiments, composites of polymer and ECM components are provided herein, as well as methods of production and use thereof. In some embodiments, composites comprise a homogeneous mixture of multiple components (e.g., ECM and polymer).

In some embodiments, a composite is prepared by combining (e.g., mixing, stirring contacting, etc.) ECM (e.g., decellularized ECM) with the monomer constituents (e.g., citric acid, diol, cysteine, etc.) of the polymer under conditions that allow for polymerization of the monomers into a polymer within the ECM, thereby creating a composite (e.g., homogeneous composite) of the polymer and ECM.

In some embodiments, a composite is prepared by combining (e.g., mixing, stirring contacting, etc.) ECM (e.g., decellularized ECM) with a pre-polymer (not significantly crosslinked, soluble, etc.) comprising the polymer constituents (e.g., citric acid, diol, cysteine, etc.) under conditions that allow for crosslinking of pre-polymer (but not the ECM) into a polymer network within the ECM, creating a composite (e.g., homogeneous composite) of the polymer and ECM.

Exemplary methods of forming a polymer/ECM composite are provided in the Examples herein. While useful for polymer/ECM composite preparation, embodiments within the scope herein are not limited to such methods.

V. Bioactive Agents

In particular embodiments exemplified herein, the bioactive agent heparin, modified to display a maleimide group (via attachment of BMPH to the heparin), is attached via click chemistry to POC-cys polymer in a composite with ECM. However, as will be appreciated by one of skill in the art, due to the nature of click chemistry reactions, which allow for pairs of selectively-reactive clicking agents to create large libraries of compounds by covalently attaching a wide array of different components, the systems and methods herein are also applicable to the attachment of other bioactive agents to polymer/ECM composites (e.g., via the same thiol/maleimide chemistry or via another suitable click pair).

As defined herein, a bioactive agent is any molecular entity which exerts a physiological, therapeutic or diagnostic effect in vivo. Bioactive agents may be naturally-occurring, modified natural entities, or synthetic/artificial agents. Representative examples include proteins, peptides, carbohydrates, lipids, nucleic acids, polymers/oligomers, anti-viral compounds, anti-inflammatory compounds, antibiotic compounds such as antifungal and antibacterial compounds, cell differentiating agents, analgesics, contrast agents for medical diagnostic imaging, enzymes, cytokines, anaesthetics, antihistamines, anticoagulants (e.g., heparin), agents that act on the immune system, hemostatic agents, hormones, angiogenic or anti-angiogenic agents, neurotransmitters, therapeutic oligonucleotides, viral particles, vectors, growth factors, retinoids, cell adhesion factors, osteogenic factors, antibodies and antigens, steroids, painkillers.

In certain embodiments, the bioactive agent is an anticoagulant or antiantithrombotic such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, etc.

In certain embodiments, the bioactive agent is a growth-promoting agent. Growth-promoting agents include any agent that functions to, for example, promote or induce cell proliferation and cell survival. Growth-promoting agents include growth factors and the like, for example: transforming growth factor-alpha (TGF-α), transforming growth factor beta (TGF-β), granulocyte-colony stimulating factor (G-CSF), granulocyte-macrophage colony stimulating factor (GM-CSF), nerve growth factor (NGF), other neurotrophins such as brain-derived neurotrophic factor (BDNF), novel neutrophin-1 (NNT-1), neurotrophin-3 (NT-3), neurotrophin-4 (NT-4); platelet-derived growth factor (PDGF), erythropoietin (EPO), thrombopoietin (TPO), myostatin (GDF-8), growth differentiation factor-9 (GDF9), acidic fibroblastgrowth factor (aFGF or FGF-1), basic fibroblast growth factor (bFGF, or FGF-2), epidermal growth factor (EGF), hepatocyte growth factor (HGF), insulin-like growth factors (IGF1, IGF2, IGF3), vascular endothelial growth factor (VEGF), human growth hormone (hGH), placental transforming growth factorbeta (PTGF-β), keratinocyte growth factor (KGF), stem cell factor (SCF), macrophage colony stimulating factor (M-CSF), pleiotrophin, amphiregulin, betacellulin, heparin-binding epidermal growth factor, heregulin (HRG), angiogenin, angiopoietin-1, angiopoietin-2, angiostatin, endostatin, platelet-derived endothelial cell growth factor, sonic hedgehog, and the like. Further examples of growth promoting agents include bone morphogenic proteins (e.g., BMP-1, BMP-2, BMP-4, BMP-6, and BMP-7) as well as members of the transforming growth factor beta (TGF-β) superfamily including, but not limited to, TGF-β1, TGF-β2, and TGF-β3; growth differentiation factors (GDF1, GDF2, GDF3, GDF5, GDF6, GDF7, myostatin/GDF8, GDF9, GDF10, GDF11, and GDF15); and bone morphogenic proteins (BMP-1, BMP-2, BMP-4, BMP-6, and BMP-7).

In some embodiments, the bioactive agent is a natural or synthetically-obtained steroid such as bryophyllin A, inotodiol, maquiroside A, ghalakinoside, mansonine, strebloside, hydrocortisone, betamethasone, and dexamethasone; or a non-steroidal substance (NSAIDS) such as fenoprofen, ibuprofen, indomethacin, naproxen, phenylbutazone, etc.

In some embodiments, the bioactive agent is an antibiotic such as cefadroxil, cefazolin, cefaclor, cefotaxim, tobramycin, gentamycin, penicillins such as dicloxacillin, oxacillin, sulfonamides, or metronidazole.

In some embodiments, the bioactive agent is a vitamin, for example, vitamin A (e.g., retinol, retinal, carotenoids (e.g., beta carotene, etc.)), vitamin B1 (e.g., thiamine), vitamin B2 (e.g., riboflavin), vitamin B3 (e.g., niacin, niacinamide), vitamin B5 (e.g., pantothenic acid), vitamin B6 (e.g., pyridoxine, pyridoxamine, pyridoxal), vitamin B7 (e.g., Biotin), vitamin B9 (e.g., folic acid, folinic acid), vitamin B12 (e.g., cyanocobalamin, hydroxocobalamin, methylcobalamin), vitamin C (e.g., ascorbic acid), vitamin D (e.g., cholecalciferol (D3), ergocalciferol (D2), etc.), vitamin E (e.g., tocopherols, tocotrienols), vitamin K (e.g., phylloquinone, menaquinones).

In some embodiments, the bioactive agent is a cytokine, chemokine, interleukin, etc. In some embodiments, the bioactive agent is a chemokine, for example, CCL1, CCL11, CCL13, CCL17, CCL18, CCL19, CCL2, CCL20, CCL21, CCL22, CCL24, CCL3, CCL5, CCL7, CCL8, CX3CL1, CXCL1, CXCL10, CXCL11, CXCL12, CXCL13, CXCL16, CXCL2, CXCL5, CXCL9, PF4, PPBP, or XCL1. In some embodiments, the bioactive agent is an interleukin, such as, IL10, IL11, IL12A, IL12B, IL13, IL15, IL16, IL17A, IL17F, IL18, IL1A, IL1B, IL1RN, IL2, IL21, IL22, IL23A, IL24, IL27, IL3, IL4, IL5, IL6, IL7, IL8, and IL9.

The bioactive agents that find use in embodiments herein are not limited to those listed above, nor to the classes of bioactive agents described herein. In some embodiments, the bioactive agent is any compound or entity that may be attached to the polymer/ECM composite via click chemistry and exerts a physiological, therapeutic or diagnostic effect in vivo.

As exemplified in experiments conducted during development of embodiments herein, in some embodiments, the bioactive agent is heparin. Heparin may be used as a monomer, oligomer, or polymer, fractionated or unfractionated; low-molecular-weight heparin; heparin sulfate; and/or any pharmaceutically-acceptable heparin form or derivative.

In some embodiments, multiple bioactive agents (e.g., 2, 3, 4, 5, 6, 7, 8, 9, 10, or more, or ranges there between) are attached to a polymer/ECM composite. For example, first and second bioactive agents, each displaying the same clicking agent, are reacted with a polymer/ECM composite displaying the clicking complement. In such embodiments, the ratio of the first and second bioactive agents incorporated into the composite is highly dependent upon the ratio of the bioactive agents provided for reaction. In other embodiments, first and second bioactive agents display different clicking moieties with different reactive complements. In such embodiments, the ratio of the first and second bioactive agents incorporated into the composite is highly dependent upon the ratio to complement clicking agents present in the composite.

VI. Clicking Groups

In particular embodiments exemplified herein, a maleimide group (BMPH) is attached to the bioactive agent and is reacted with a thiol displayed on a POC-cys polymer in a composite with ECM. However, as will be appreciated by one of skill in the art, other click chemistry pairs may find use in attaching binding agents to polymer/ECM composites. Exemplary pairs of clicking groups include, but are not limited to thiol and maleimide groups, alkyne and azide groups, transcyclooctene and tetrazine groups, dibenzocyclooctyne and azide groups, etc. Embodiments herein are not limited by which agent of the click chemistry pair is attached to the bioactive agent and/or the polymer. Other functional-group pairs capable of click chemistry may also be used.

In some embodiments, in order to utilize other click chemistry pairs, a first clicking agent is attached to a bioactive agent, and the complement clicking agent is incorporated into a polymer, or appended onto a polymer, that is used to form a composite with ECM. The selective reactivity of the click chemistry pair allows for attachment of the bioactive agent to the polymer of the polymer/ECM composite.

In some embodiments, in addition to the covalent attachment of a bioactive agent to the polymer/ECM composite, one or more bioactive agents are mechanically entrapped within the composite and/or non-covalently associated therewith. In some embodiments, formation of the composite involves the filling of the spaces within the ECM with pre-polymer, which is, in turn, polymerized within the ECM to form the composite. In some embodiments, the interweaving of the polymer and ECM into a homogeneous material results in a complex network of channels through the composite. In some embodiments, bioactive agents not covalently attached to the polymer composite are entrapped within the composite network, and can subsequently be released (e.g., over time) upon exposure of the composite to aqueous and/or physiologic conditions. In some embodiments, bioactive agents are entrapped within a composite by soaking the formed composite in a solution or mixture comprising the bioactive agent. In some embodiments, bioactive agents are added to the bioactive agent and/or polymer/ECM prior to composite formation and are then entrapped upon formation of the complex.

VII. Applications

Embodiments herein find use in, for example: anticoagulation in decellularized organs, (e.g., vascular grafts, hearts, livers, kidneys, etc.), anticoagulation in re-cellularized organs (e.g., that are not 100% covered with cells before implantation), heparin binding growth factor (e.g., Fibroblast growth factor, epidermal growth factor) delivery and presentation in ECM-based biomaterials for tissue engineering applications, etc.

Embodiments herein provide advantages over existing technologies. For example, existing technologies to immobilize heparin to ECM involve chemical crosslinking of ECM with reagents such as glutaraldehyde and EDC/NHS, which are toxic and can significantly alter ECM ultrastructure and mechanical properties.

Embodiments herein, for example, POC-Cys-BMPH-Heparin conjugate, does not require crosslinking of ECM, thus eliminating potential alternation in ECM properties.

Another existing technology to bind heparin onto ECM is to use chitosan. Using a cationic polymer as intermediate, heparin is added to chitosan layer by layer through ionic binding. Embodiments herein utilize covalent binding, which is more stable than ionic link in physiological environments. Moreover, chitosan is thrombogenic and causes additional blood coagulation if exposed to blood. Embodiments herein eliminate the use of chitosan and are therefore safer than methods involving chitosan or other cationic polymers.

EXPERIMENTAL

Example 1

Synthesis of Heparin-BMPH

Heparin was covalently linked to BMPH using standard carbodiimide chemistry (FIG. 1). Briefly, heparin sodium (average Mw 15 k Da, Celcus, Cincinnati, Ohio) was dissolved in a buffered solution of 0.05M 2-morpholinoethanesulfonic acid (MES, pH 6) at 1 mM. BMPH (N-[β-maleimidopropionic acid] hydrazide, trifluoroacetic acid salt), Mw 297.19 g/mol, Pierce™) was dissolved in the same solution at 10 mM (10× molar ratio of heparin). N-hydroxy-succinimide (NHS, 60 mM; Sigma) and 1-ethyl-3-(3-dimethylaminopropyl)-carbodiimide hydrochloride (EDC, 120 mM; Sigma) were added to the solution to activate the carboxylic acid groups of the heparin. After 2 h of reaction at room temperature with constant stirring, the product was dialyzed against water with a porous membrane (3500 MWCO) to removed unreacted BMPH overnight and then lyophilized to dry for 3 days. The success conjugation of BMPH onto heparin can be confirmed with H-NMR (peak 6.74 ppm, -H on maleimide group). The bioactivity of heparin after BMPH conjugation was compared with heparin sodium solution using a Factor Xa assay kit, which showed no change in heparin bioactivity due to BMPH conjugation.

Synthesis of POC-Cys Prepolymer

The synthesis and characterization of POC-Cys was described by Yang et al (Yang et al., PNAS, 2009). Briefly, 1,8-octanediol, citric acid and L-cysteine (molar ratio 1:1:0.2) were mixed at 140° C. and reacted for 1 hour. The product was firstly dissolved in ethanol and then precipitated in deionized water to removed unreacted monomers and low molecular weight polymers. The precipitation was lyophilized to dry and dissolved in ethanol at 30 wt % as stock solution. The success conjugation of L-cystein onto POC prepolymer can be confirmed with H-NMR (peak at 1.02 ppm, H on thiol group).

Post-Polymerization of POC-Cys onto ECM

Rat aortas were harvested and decellularized using a sequential combination of Triton X-100 and sodium dodecyl sulfate, followed by a nuclease treatment. Decellularized rat aorta was used as an example of ECM. The POC-Cys pre-polymer was diluted with absolute ethanol to 1% (w./w.) prior to applying ECM. Decellularized aorta was firstly dehydrated with ethanol and then incubated in 1% pre-polymer solution for 30 min with continuous stirring. The pre-polymer infused ECM was then post-polymerized at 37° C. or 45° C. for 4 days to allow ester-bond crosslinks formation among POC pre-polymers. The hybridized POC-ECM composites were rinsed with PBS at 37° C. for 3 days to allow the removal of unbounded low molecular weight POC-Cys pre-polymers. POC-Cys coated ECM showed blue fluorescence (FIG. 2.B) comparing to non-coated ECM (FIG. 2.A), due to auto-fluorescence of POC-Cys.

Reaction of Heparin-BMPH with POC-Cys-ECM Composite

Figure 3A:
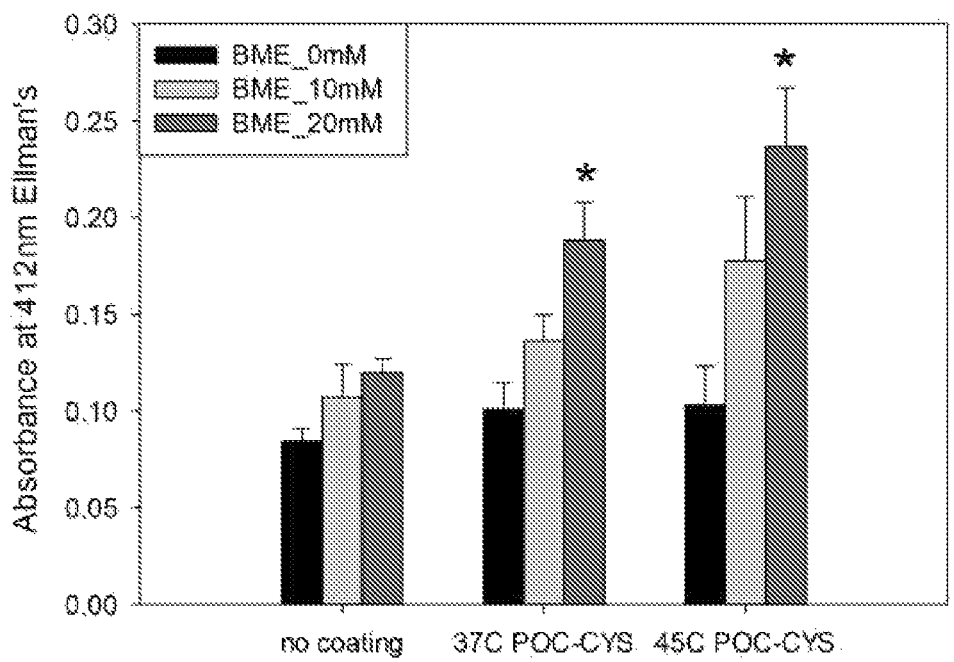
FIGS. 3A-B show graphs depicting the quantification of —SH group (A) and elastic modulus (B) of ECM-POC-Cys composites treated with BME solutions. * indicates significant difference (p<0.05).
Figure 3B:
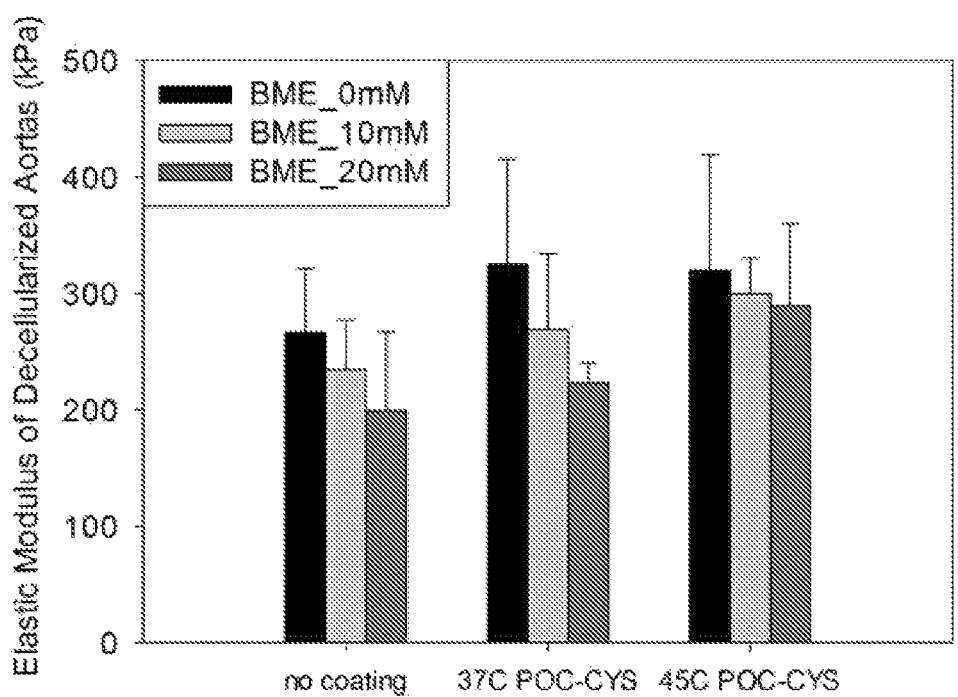

The polymer-ECM composite or ECM itself was firstly treated with 2-mercaptoethanol (BME) for 1 hour at room temperature to breakdown disulfide bonds that were formed during post-polymerization. The free thiol groups on ECM were quantified with Ellaman's reagent before and after BME treatment. Tensile tests were performed on aortas before and after decellularization (n=3) using Instron 5544 Materials Testing Machines (Instron, Norwood, Mass.). At 20 mM, BME frees more thiol groups from POC-Cys coating (FIG. 3.A), without significantly altering ECM mechanical properties (FIG. 3.B). After rinsing with PBS to remove residual BME, the ECM was then incubated in 10 mg/ml heparin-BMPH solution overnight with continuous stirring, to allow BMPH to react with free thiols on POC-Cys coated ECM, thus linking heparin onto ECM.

Severe Intimal Hyperplasia Formation in Heparin Modified Crosslinked Decellularized Arteries in a Rat Model Experiments were conducted during development of embodiments of the present invention to evaluate the engineered polymer-ECM composite vascular graft in an animal model. The effects of POC coating, heparin conjuration, and change in crosslink density of ECM are evaluated using a rat abdominal aorta interposition model.

Animal Surgery

A rat abdominal aorta interposition model was used to evaluate decellularized aorta as vascular graft. All animal experiment procedures were approved by NU-IACUC. The abdominal aorta was excised and replaced with a segment (1 cm in length) of decellularized aorta graft of various modifications.

Post-Surgical Evaluation

Tissue harvest: Four weeks after the implantation surgeries, the animals were sacrificed and the grafts with both anastomoses removed. Each graft was divided into five regions from the proximal to the distal end, with 2 mm per segment.

Histological Staining and Analysis

The sections were stained with H&E and Masson's trichrome staining. Intimal hyperplasia thickness and area were analyzed from those staining images. Immunofluorescence staining for eNOS (endothelial cell marker), α-SMA (smooth muscle cell marker) and CD68 (macrophage marker) were performed using indirect methods. Percent endothelial cell coverage and inflammatory cell density were analyzed from those images.

Functional and Structural Analysis

Experiments were conducted during development of embodiments in which the above method was optimized (although other embodiments of the above strategy are within the scope herein) on 96-well plates and then applied to decellularized rat aortas as a model ECM. The structure of POC-Cys pre-polymer and heparin-BMPH was confirmed with H-NMR. POC-Cys (1 wt % in ethanol) pre-polymer was coated onto 96-well plates and post-polymerized at 80° C. for 4 days, or onto ECM and post-polymerized at 37° C. or 45° C. for 4 days. The surfaces were then treated with 2-mercaptoethanol (BME) to breakdown disulfide bonds. Free thiol groups were measured with Ellman's reagent. The surfaces with free thiols were then reacted with heparin-BMPH solutions overnight. The heparin bioactivity was measured with a Factor Xa kit. Tensile testing was used to measure changes in ECM elastic modulus due to the modifications.

Figure 2:
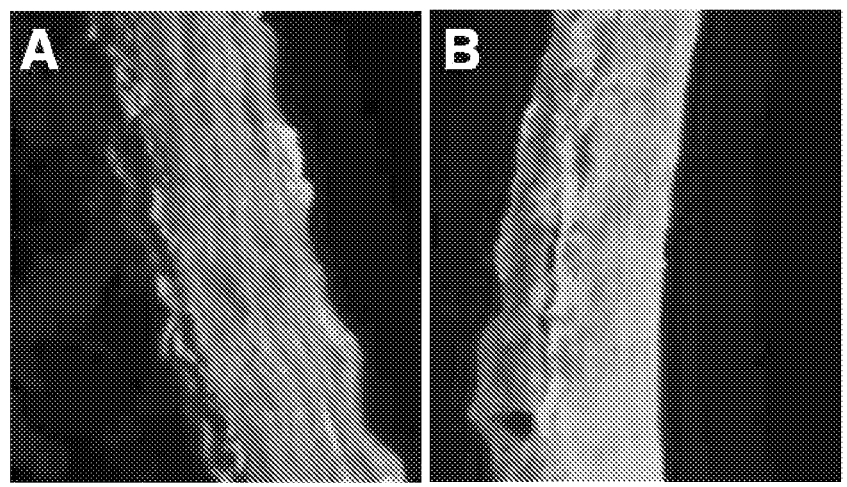
FIG. 2 shows images of decellularized aorta without (panel A) and coated with (panel B) POC-Cys. The coated aorta exhibits florescence.
Figure 4A:
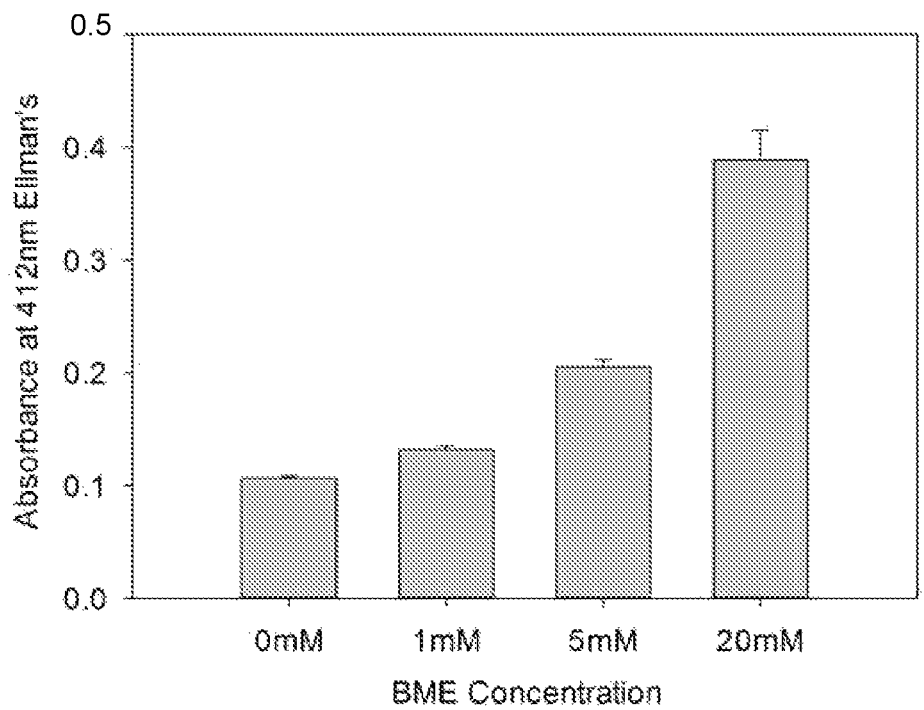
FIGS. 4A-B show graphs depicting an Ellman's assay showing increased available —SH groups with increasing BME concentration for POC-Cys coated 96-well plates (A) and decellularized aortas (B).
Figure 4B:
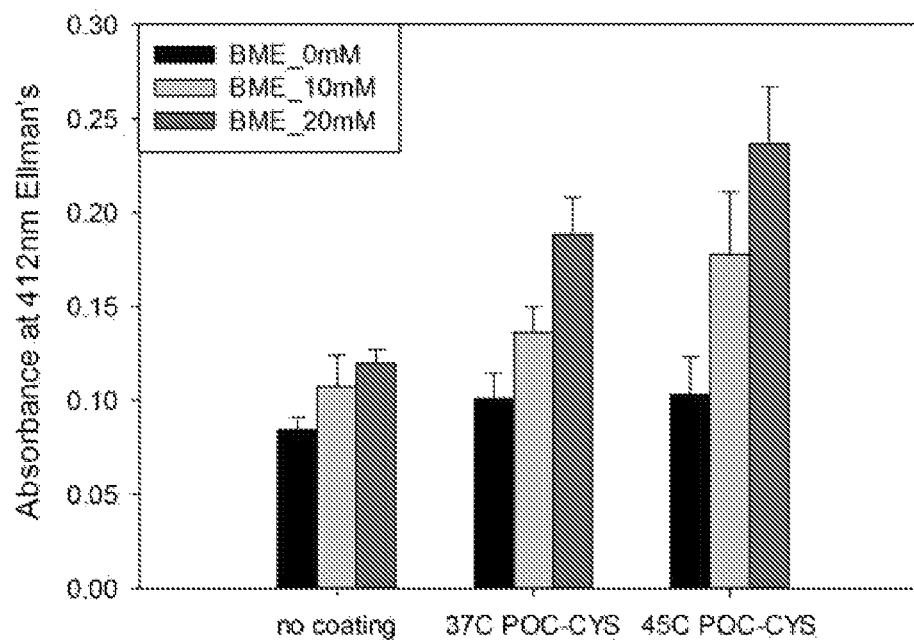
Figure 5A:
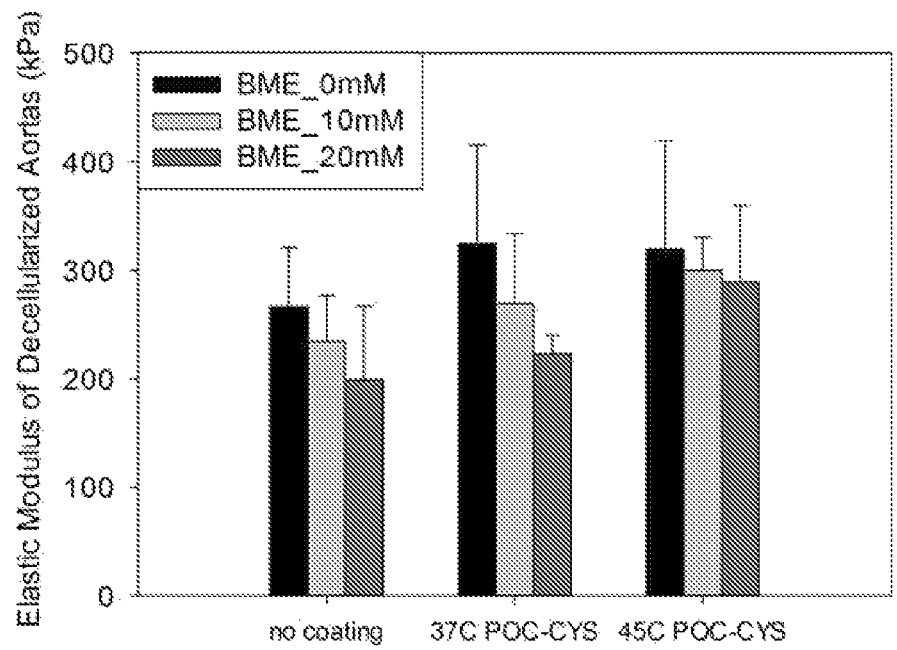
FIGS. 5A-B show graphs demonstrating that tensile tests of decellularized aortas showed no significant change in elastic modulus with POC-Cys coating and BME treatment (A), as opposed to significant increase in stiffness after NHS/EDC crosslinking (B).
Figure 5B:
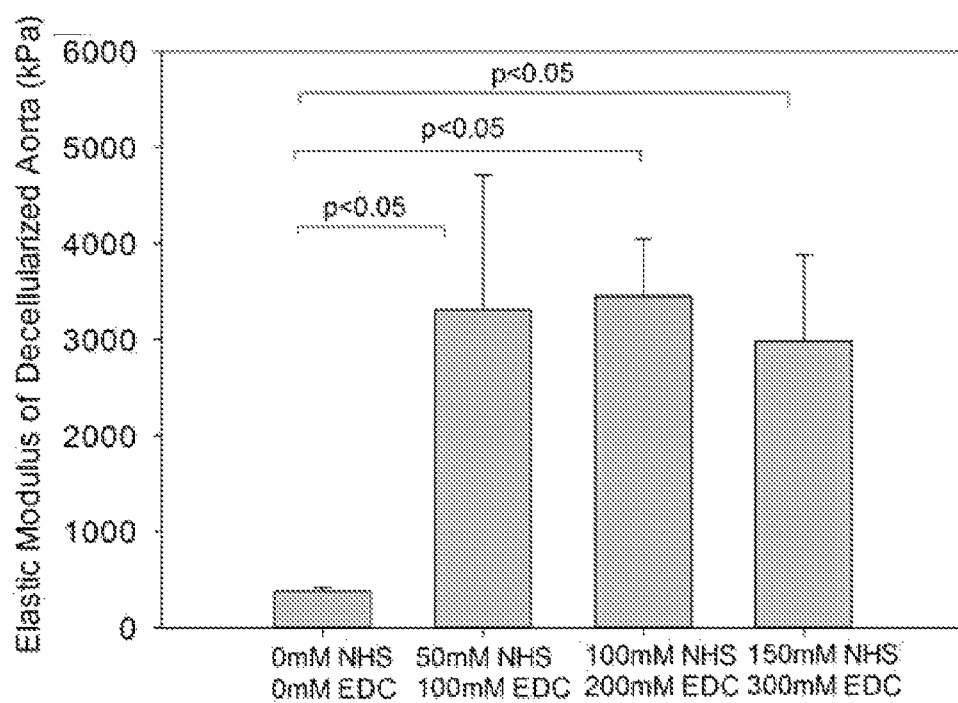
Figure 6A:
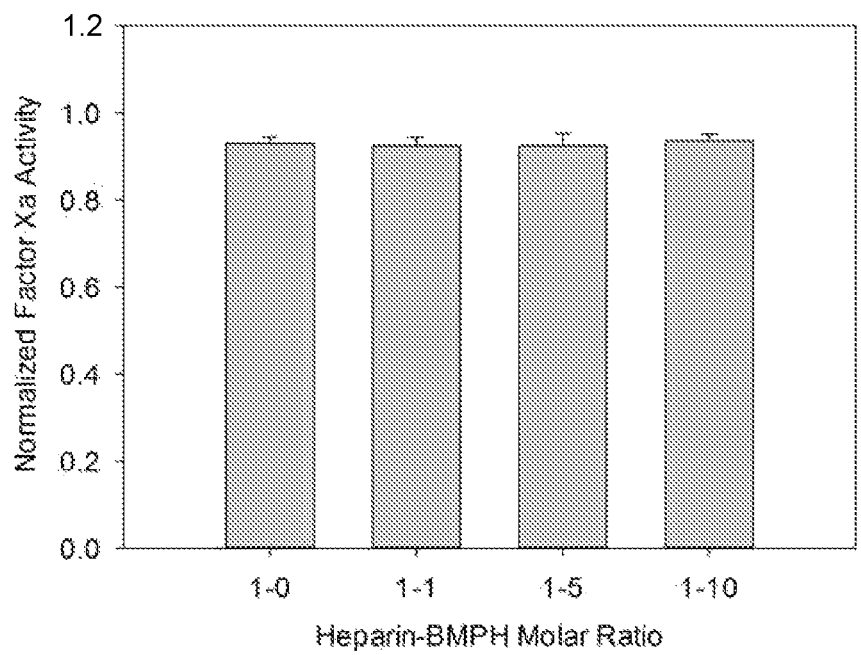
FIGS. 6A-B show graphs demonstrating Factor Xa activity analysis for heparin-BMPH in solution (A) and on POC-Cys coated surfaces (B).
Figure 6B:
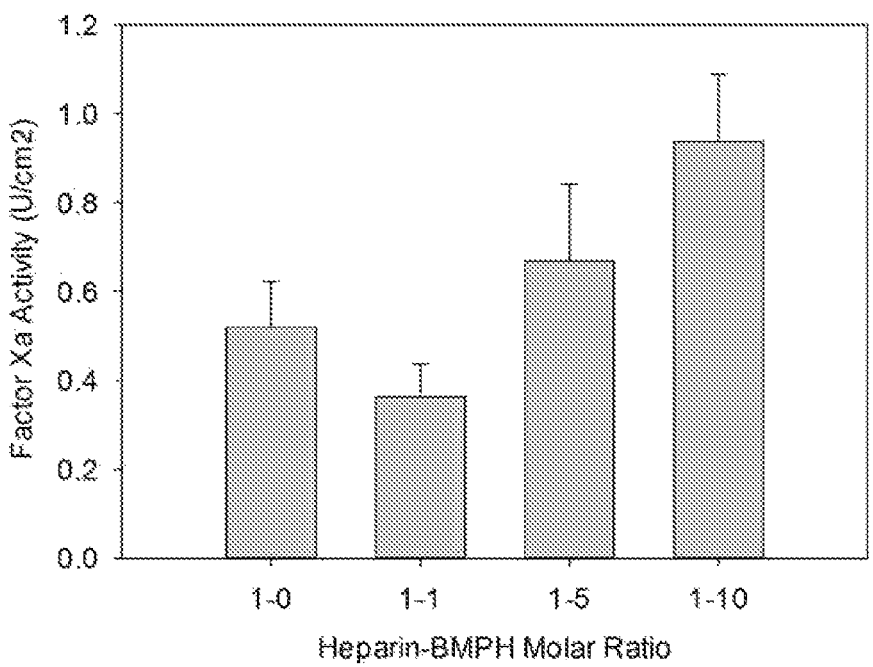
Figure 7:
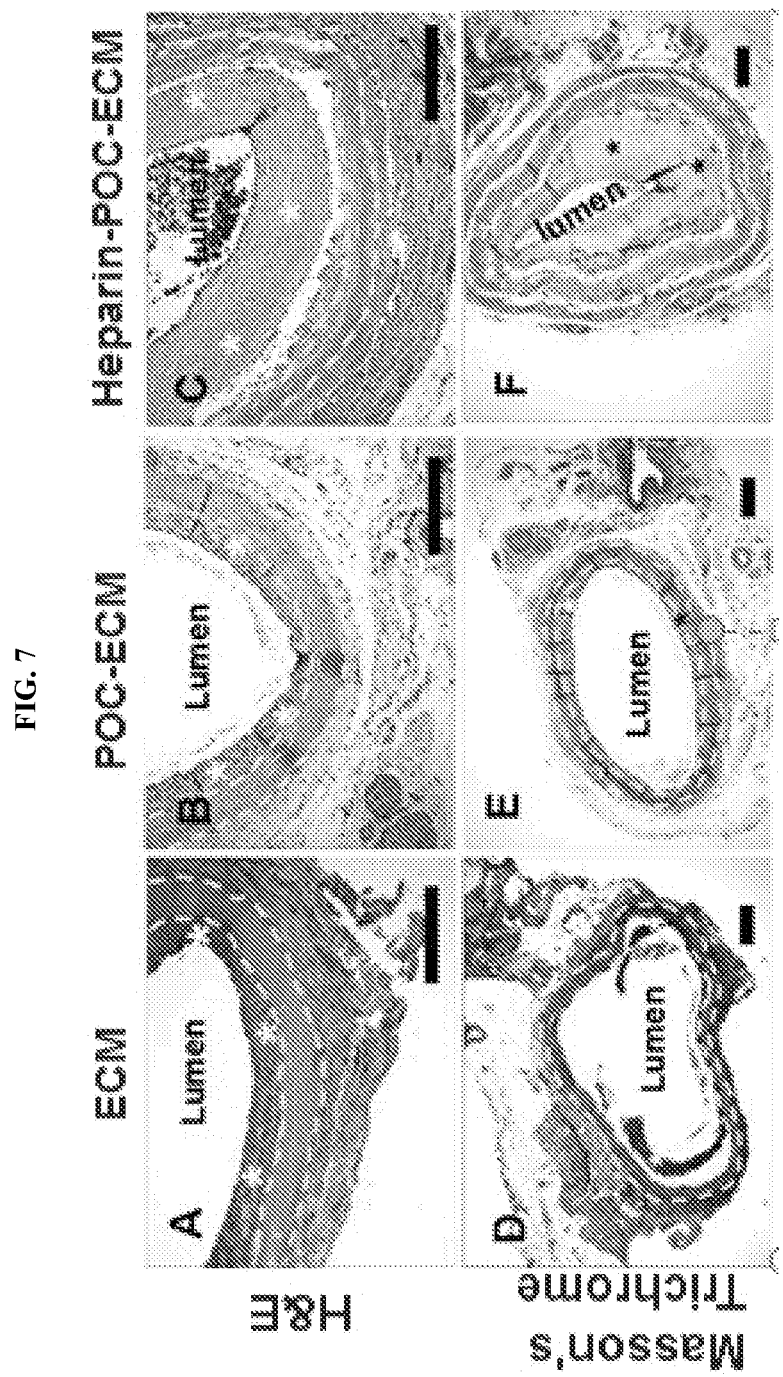
FIG. 7 shows images of H&E (panels A, B, C) and Masson's trichrome (panels D, E, F) staining of decellularized aorta with various treatments. All grafts were harvested from rat aorta interposition model at 4 weeks after implantation. Severe intimal hyperplasia was observed for heparin conjugated ECM, contrary to in vitro results. Grafts were outlined between dashed lines, while * indicates the presence of intimal hyperplasia. Scale bar=200 μm.
Figure 8:
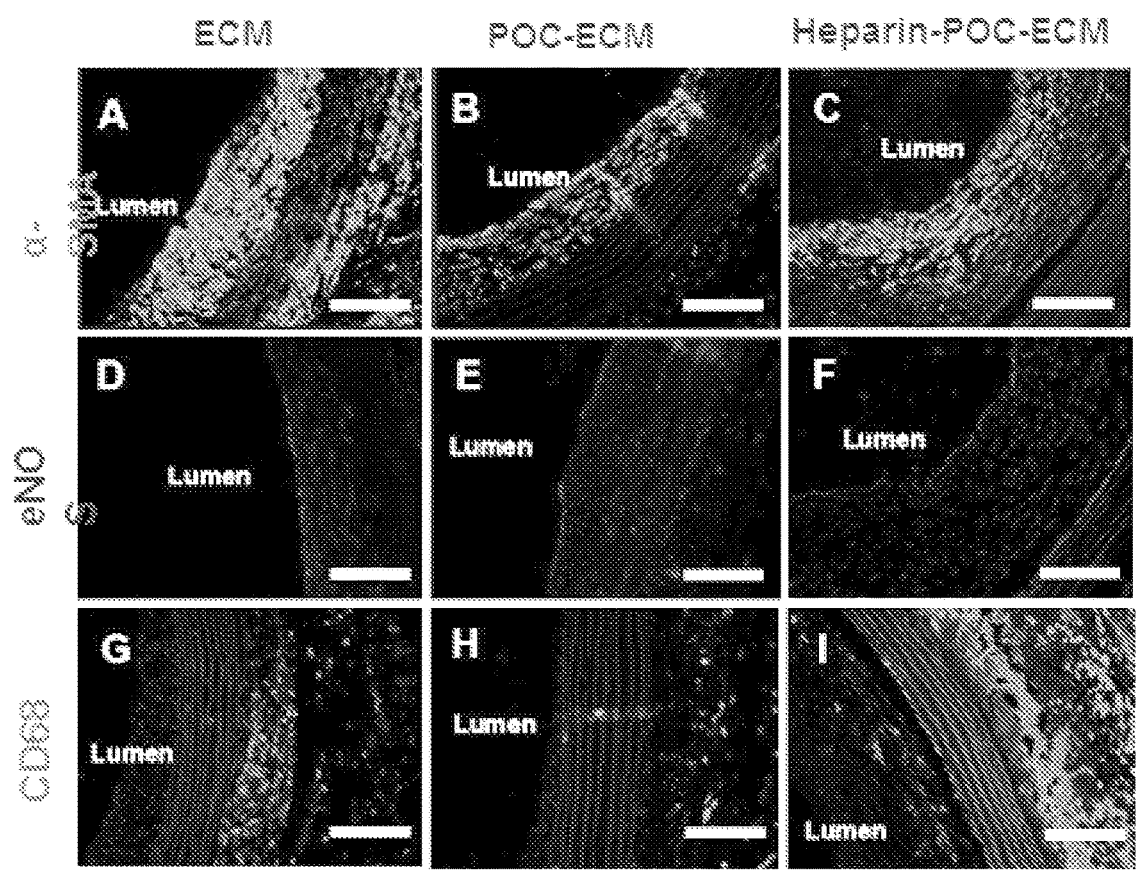
FIG. 8 shows immunofluorescence staining of α-SMA (panels A, B, C), eNOS (panels D, E, F) and CD 68 (panels G, H, I) for decellularized aorta of various treatment. All grafts were harvested from rat aorta interposition model at 4 weeks after implantation. Scale bar=100 μm.
Figure 9A:
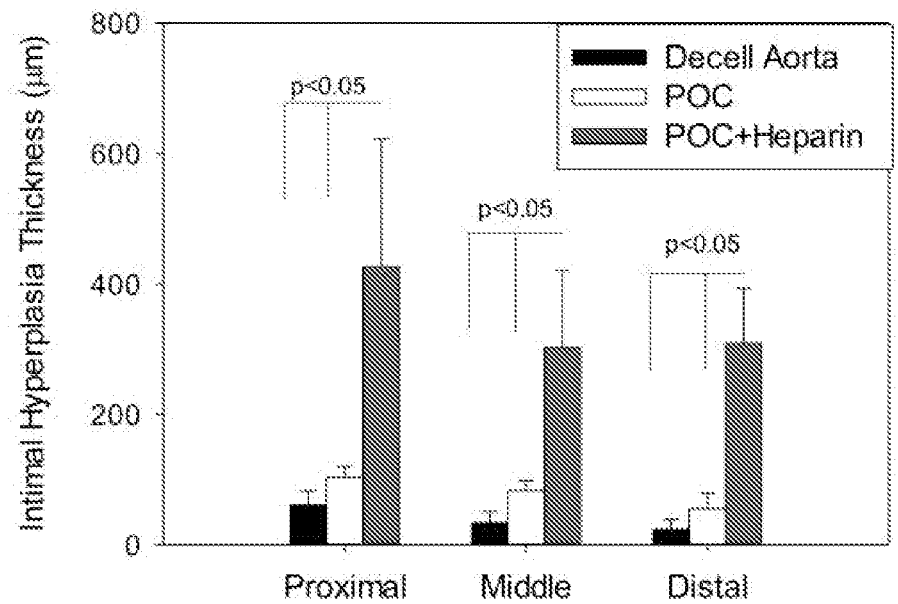
FIGS. 9A-D show quantitative analysis for the thickness of intimal hyperplasia (A), area of intimal hyperplasia (B), endothelial cell coverage (C) and macrophage cell density (D). Data were analyzed at proximal, middle and distal section of implanted grafts 4 weeks after surgery. Significant increase in intimal hyperplasia thickness and area, and CD68 density was observed after heparin conjugation, indicating poor biocompatibility.
Figure 9B:
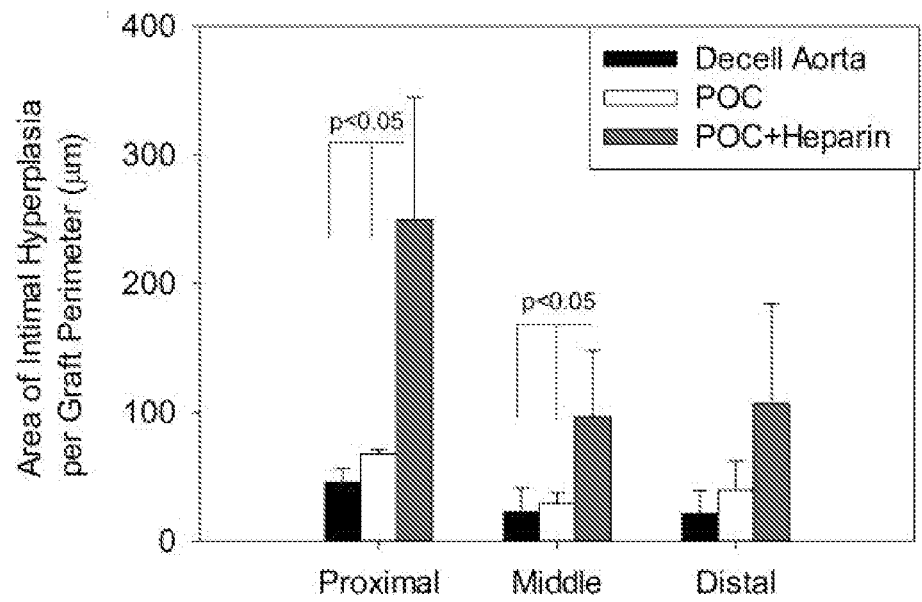
Figure 9C:
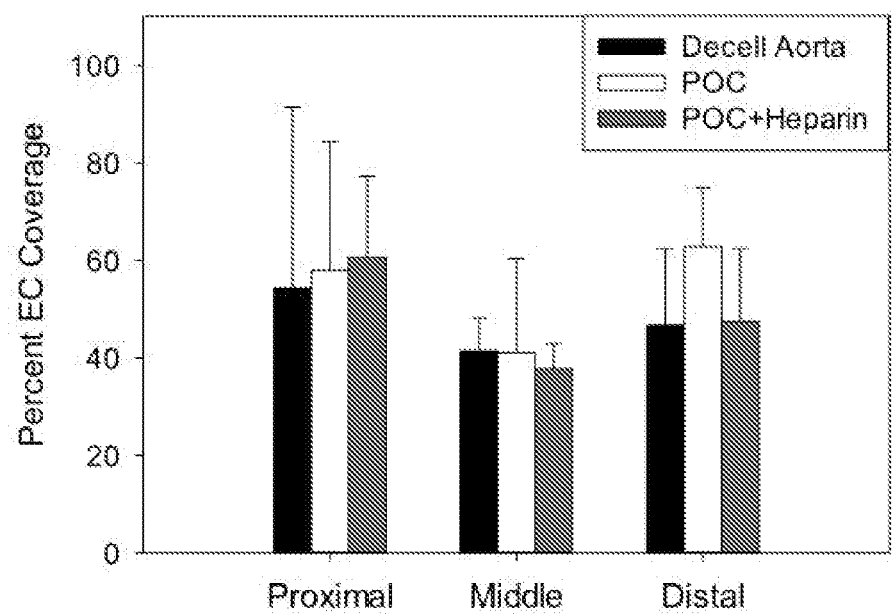
Figure 9D:
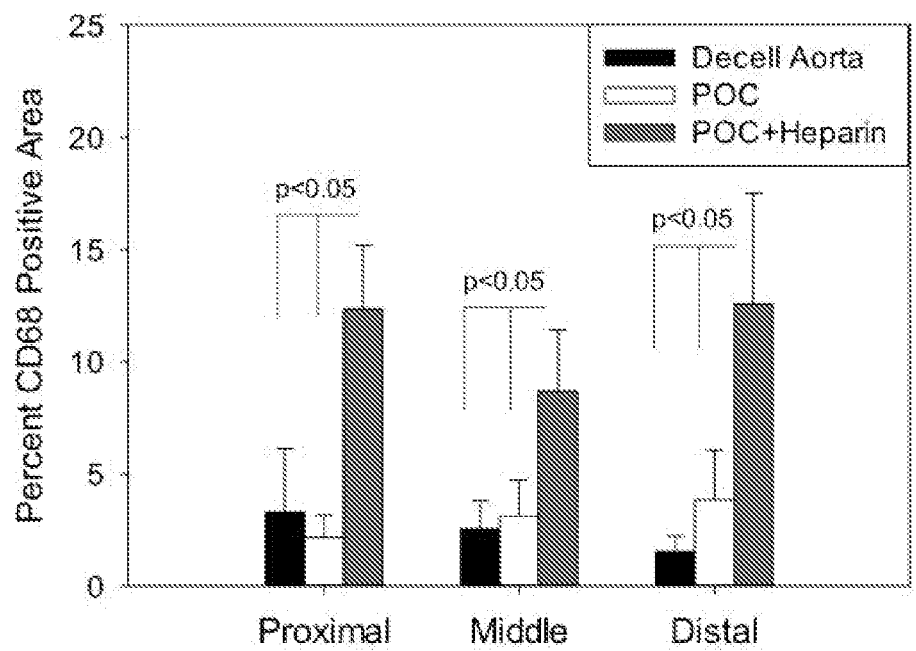

H-NMR confirmed the structure of POC-Cys (peak at 1.02 ppm, —SH group), and the structure of heparin-BMPH (peak 6.74, —H on maleimide). POC-Cys exhibited autofluorescence under UV light (FIG. 2). POC-Cys coating provided —SH groups on coated surfaces, which formed di-sulfide bonds during post-polymerization. The di-sulfide bonds were broken down to free —SH groups with BME on both plastic surfaces (FIG. 4.A) and ECM (FIG. 4.B). Treating decellularized aortas with POC-Cys or BME did not alter the ECM elastic modulus (FIG. 5.A) significantly, when compared to EDC/NHS chemistry, which increased ECM stiffness by more than 5 fold (FIG. 5B). Factor Xa activity analysis for heparin-BMPH in solution showed no change in heparin bioactivity due to BMPH conjugation (FIG. 6A). POC-Cys-coated surfaces (80° C. plastic, 20 mM BME treatment) exhibited an increase in heparin activity with increasing ratio of BMPH (Heparin:BMPH=1:10). (FIG. 6B).

Example 2A

Materials and Methods

Animals

Male Sprague Dawley rats (200-250 g) were used as donors and recipients for abdominal aorta recovery and implantation. Animal care was performed in accordance with the NIH Guide for Care and Use of Laboratory Animals, and all experiments using animals were approved by the Animal Care and Use Committee of Northwestern University.

Heparinization of Polymer-ECM Composites

Reagents were purchased from Sigma-Aldrich (St. Louis, Mo.) unless specified otherwise.

Figure 10A:
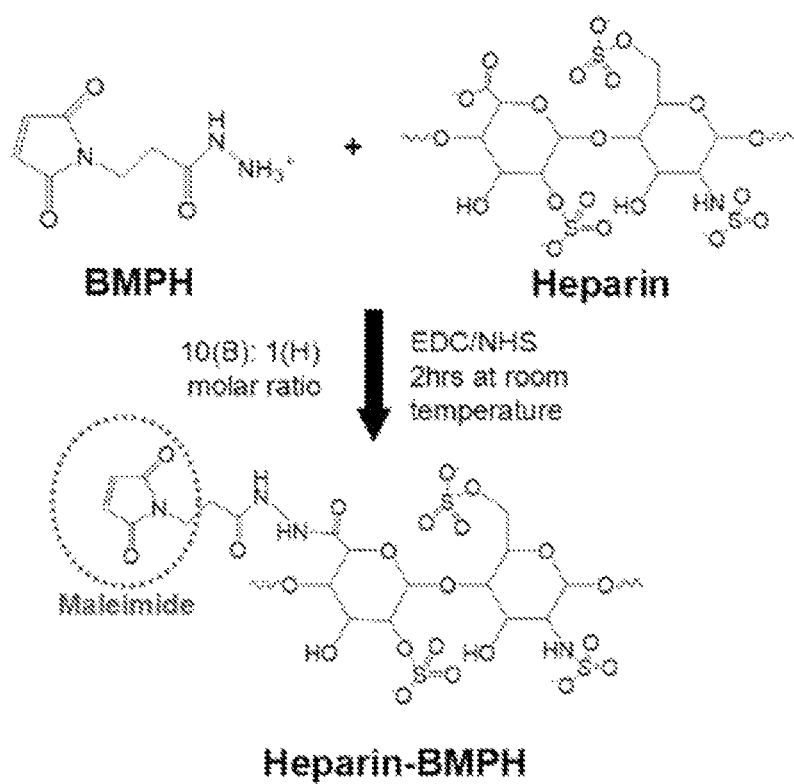
FIGS. 10A-C show a schematic representation of heparinized mechanocompatible polymer-ECM composite formation. (A) Heparin was conjugated with BMPH (containing maleimide group) using carbodiimide chemistry. (B) POC-Cys prepolymer was synthesized with 1,8 octanediol, citric acid and cysteine (e.g., 1:1:0.2 molar ratio) and hybridized onto ECM to form polymer-ECM composites with additional thiol groups. (C) Maleimide-thiol "click" chemistry between heparin-BMPH and polymer-ECM composite to immobilize heparin onto ECM.

Heparin functionalization with maleimide group (FIG. 10A). Heparin sodium salt (200 U/mg, Celsus Laboratories, Cincinnati, Ohio) was dissolved in MES buffer (pH 6.5) at 1 mM, with 60 mM N-hydroxysuccinimide (NHS) and 120 mM 1-Ethyl-3-(3-dimethylaminopropyl)carbodiimide (EDC). N-β-maleimidopropionic acid hydrazide (BMPH, 10 mM) was reacted with heparin for 2 hours at room temperature, to allow conjugation of heparin (—COOH) with BMPH (—NH$_2$). The product was dialyzed against Milli-Q water with MWCO 3500 membrane and lyophilized to dry. The amount of maleimide group per mol of heparin was quantified by Ellman's reagent assay [ref 43; herein incorporated by reference in its entirety] after reacting with excessive L-cysteine solution.

Figure 10B:
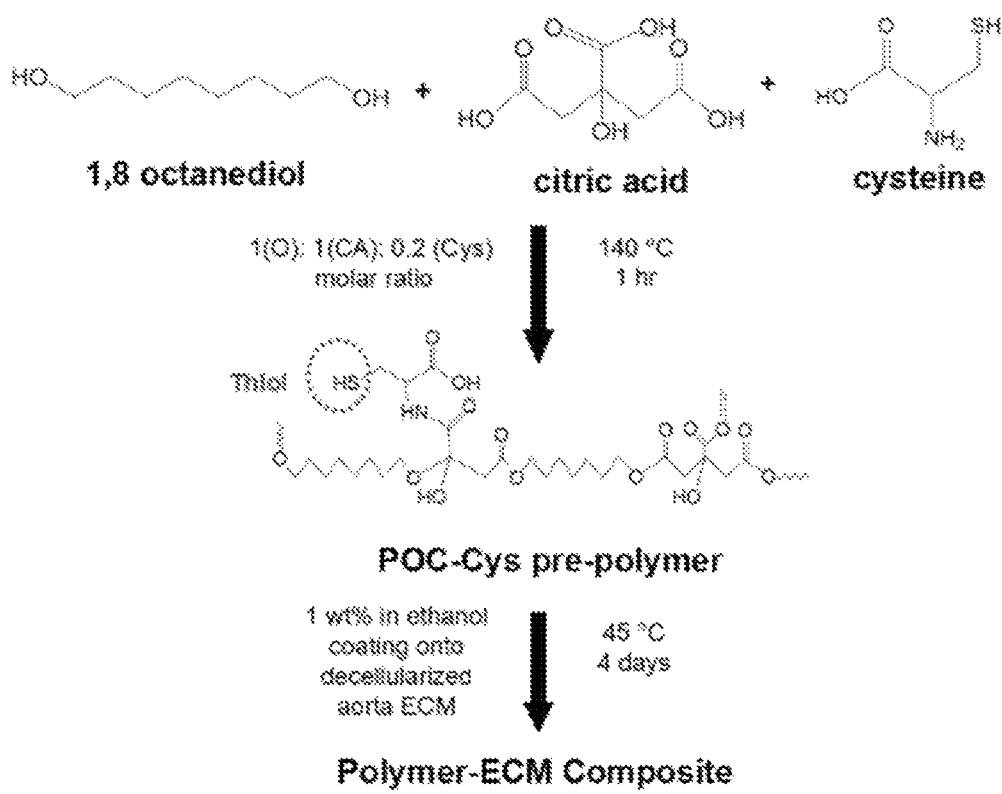

Polymer-ECM composite preparation (FIG. 10B). Decellularization of rat abdominal aortas was performed as described [ref 5; herein incorporated by reference in its entirety]. POC-Cys prepolymer (molar ratio of 1,8-octanediol, citric acid and cysteine 1:1:0.2) was synthesized as described [ref 13; herein incorporated by reference in its entirety]. The POC-Cys pre-polymer was diluted with absolute ethanol to 1% (w./w.). Decellularized aorta ECM was firstly dehydrated with ethanol and then incubated in 1% pre-polymer solution for 30 min with continuous stirring. The pre-polymer infused ECM was then post-polymerized at 45° C. for 4 days, then incubated with PBS at 37° C. for 3 days to remove unbound prepolymer. Prior to "click" chemistry, the polymer-ECM composites were treated with 20 mM 2-Mercaptoethanol (BME) for 1 hour at room temperature to free thiol groups provided by POC-Cys polymer, after which the samples were rinsed extensively with PBS to remove BME. The amount of free thiol groups present on polymer-ECM composites were quantified via Ellman's reagent assay and normalized to tissue weight.

Figure 10C:
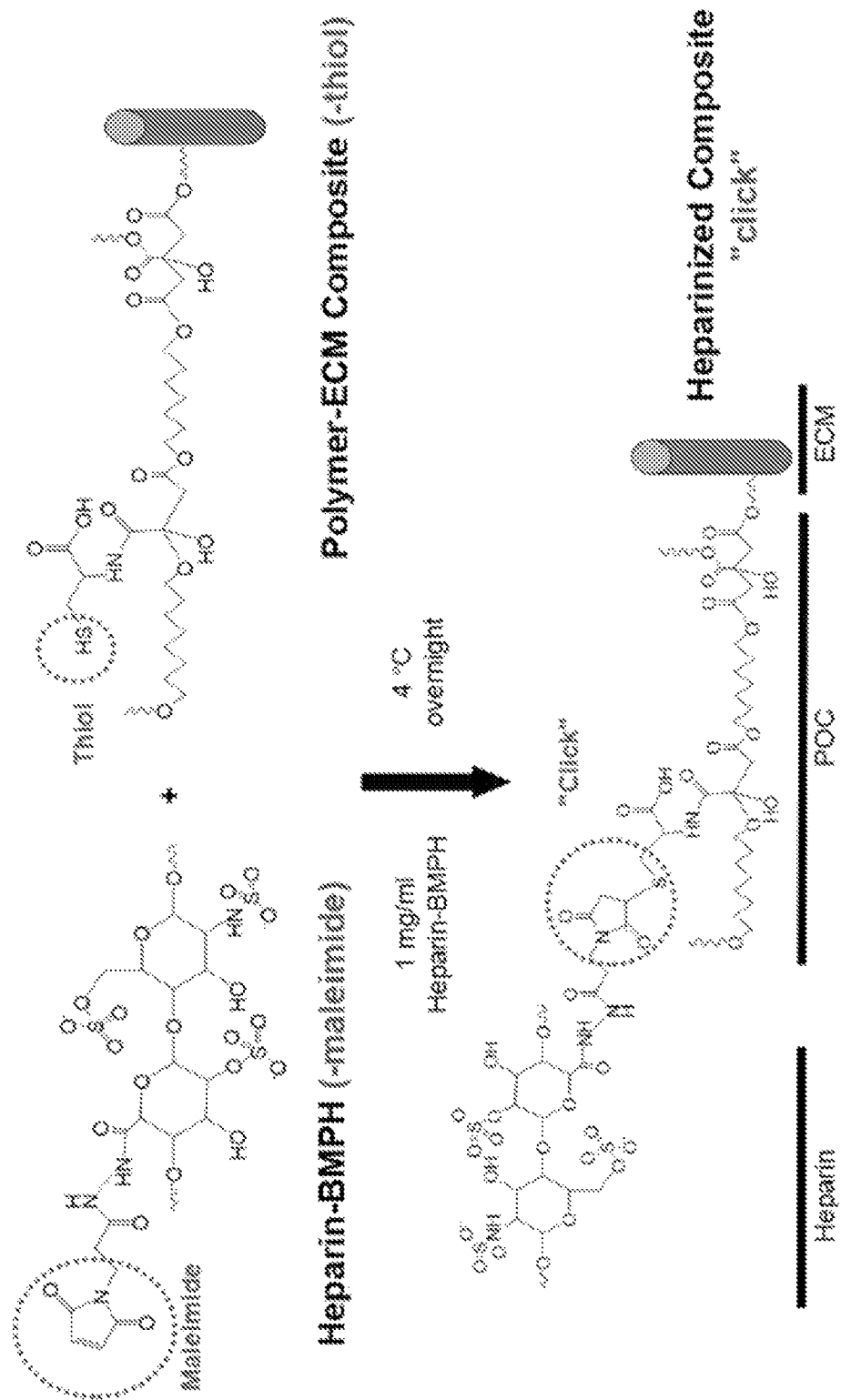

Maleimide-thiol "click" chemistry (FIG. 10C). The polymer-ECM composites were incubated in heparin-BMPH solution (1 mg/ml in PBS) overnight to allow diffusion of heparin-BMPH throughout the entire polymer-ECM scaffold. Three washes with PBS were performed to remove unbound heparin.

Evaluation of Heparinized Polymer-ECM Composites in Vitro

Heparin quantification. A dimethylmethylene blue (DMMB) based glycosaminoglycan (GAG) assay (ref. 44; herein incorporated by reference in its entirety] was used to quantify heparin concentration on ECM. Briefly, ECM samples were weighed first and then treated with Proteinase K (15 U/ml) at 60° C. overnight to digest the entire ECM scaffold. The digested samples were added to DMMB solution for colormetric measurement, in comparison with heparin serial dilutions as standard curve. ECM samples without heparin modification served as controls to provide background GAG concentration value.

Platelet adhesion. A platelet adhesion assay (ref 5; herein incorporated by reference in its entirety] was performed on ECM samples to evaluate their anti-throbogenic properties after heparin modification.

Mechanical tests. A tensile test was performed for native rat aorta, decellularized rat aorta ECM, and heparinized rat aorta ECM using either "click" chemistry or crosslinking chemistry, and their elastic moduli calculated as described previously (ref 5; herein incorporated by reference in its entirety].

Evaluation of Heparinized Polymer-ECM Composites in Vivo

Figure 13:
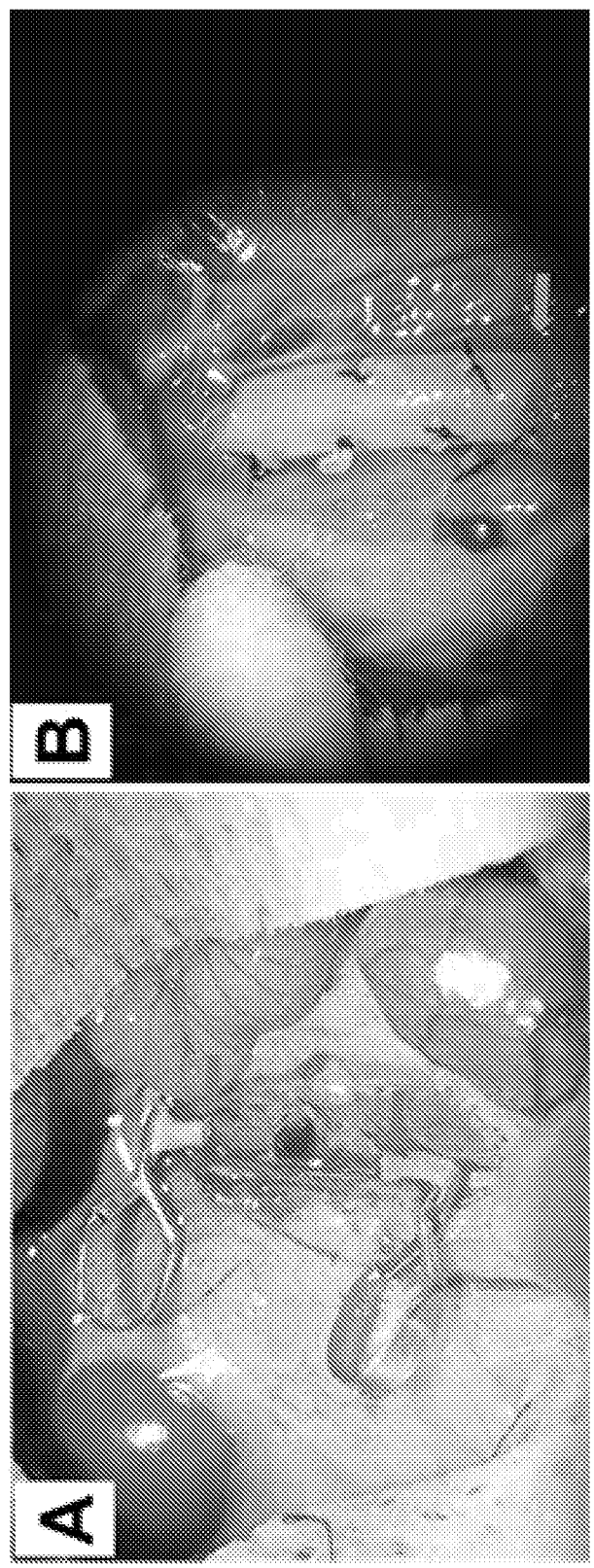
FIG. 13 shows images of the rat abdominal aorta interposition model used to evaluate rat ECM based vascular grafts. (panel A) Prior to implantation, the abdominal aorta was clamped in both proximal and distal regions using micro-vessel clips and a segment (1 cm) of native artery was excised between the clips. (panel B) A segment (1 cm) of decellularized aorta ECM graft was connected to the native aorta using an end-to-end anastomosis at each end. Branches of aorta grafts were tied up with silk sutures and anticoagulant meshes were used at the proximal and distal ends to prevent bleeding.

Surgery. A rat abdominal aorta interposition model was used to evaluate decellularized aorta as vascular graft. Briefly, Male Sprague Dawley rats (200-250 g) were anesthetized by isoflurane inhalation (1-5%) using VetEquip inhalation anesthesia system. The abdomen of the anesthetized rat was entered through a midline incision. The abdominal aorta was exposed and clamped in both proximal and distal regions using micro-vessel clips and then is excised between the clamps (FIG. 13A). A segment (1 cm in length) of decellularized aorta graft (ECM control, polymer-ECM composite, heparinized composite via "click" chemistry, and heparinized composite via crosslinking) was connected to the abdominal aorta using an end-to-end anastomosis technique with interrupted stitches at each end. Branches of aorta grafts were tied with silk sutures to prevent bleeding (FIG. 13B). Following reperfusion of blood flow through the graft, the incision was closed in layers. Ultrasound imaging technique with and without Doppler was performed to monitor graft patency weekly, using an M7/M7T Diagnostic Ultrasound System (Mindray Bio-Medical Electronics, Shenzhen, China) with an L14-6S probe.

Histological and Immunofluorescence Staining. Four weeks after the implantation surgeries, the animals were sacrificed and the grafts excised including both anastomoses and fixed in 4% formaldehyde solution. Each graft (1 cm long) was divided into five regions from the proximal to the distal end, including the two anastomoses sites, with 2 mm per segment. Each segment was embedded in paraffin and sectioned with a microtome with 5 µm thickness. The sections were stained with H&E, Masson's trichrome and von Kossa stainings after deparaffinization and rehydration following standard protocols. Bright field microscopy was then used to image the sections with 4× and 10× objective (Nikon TE2000U, Melville, N.Y.). Immunofluorescence staining for eNOS (endothelial cell marker), α-SMA (smooth muscle cell marker) and CD68 (macrophage marker) was performed. Primary antibody (eNOS, α-SMA or CD68, 1 ug/ml in 5% goat serum, Santa Cruz) was added to the sections and incubated in a humid chamber overnight at 4° C. After washing with PBS, the sections were then incubated with fluorescence conjugated secondary antibody (4 ug/ml in 5% goat serum) for 2 hours at room temperature. All immunofluorescence staining slides were imaged with fluorescence microscopy. (Nikon TE2000U, Melville, N.Y.).

Evaluation. The histological and immunofluorescent images were analyzed for the degree of intimal hyperplasia, endothelial coverage and inflammation with ImageJ (National Institute of Health, Bethesda, Md.). To quantify the degree of intimal hyperplasia, the ratio of the area of intimal hyperplasia (α-SMA positive region) to the circumference of the graft ($\mu m^2/\mu m$ graft circumference) was calculated as previously described (ref 45; herein incorporated by reference in its entirety). Endothelial coverage was defined as the circumferential length of the endothelial cell layer (eNOS positive) on the inner surface, and expressed as the percentage of total graft circumference. Inflammation was analyzed by calculating the area of macrophages (CD68 positive) per area of tissue surrounding the vascular graft.

Statistical Analysis

All statistical data are expressed as means±standard deviation. Data were analyzed using one way ANOVA with a Tukey-Kramer post-test using SigmaStat (San Jose, Calif.). For all comparisons, $p<0.05$ was considered statistically significant.

Example 2b

Results

Heparin Functionalization and Polymer-ECM Composite Preparation

Decellularized rat abdominal aortas were used as vascular ECM scaffolds, and heparin was immobilized onto ECM (FIG. 10): (A) conjugating (N-[ε-maleimidopropionic acid] hydrazide) (BMPH) to heparin to add maleimides onto heparin; (B) hybridizing the decellularized aorta ECM with poly(1,8-octamethylene)-co-cysteine (POC-Cys) to add thiols to the ECM; (C) reacting heparin-BMPH with polymer-ECM composites via "click" chemistry to ultimately link heparin to the ECM.

Figure 11A:
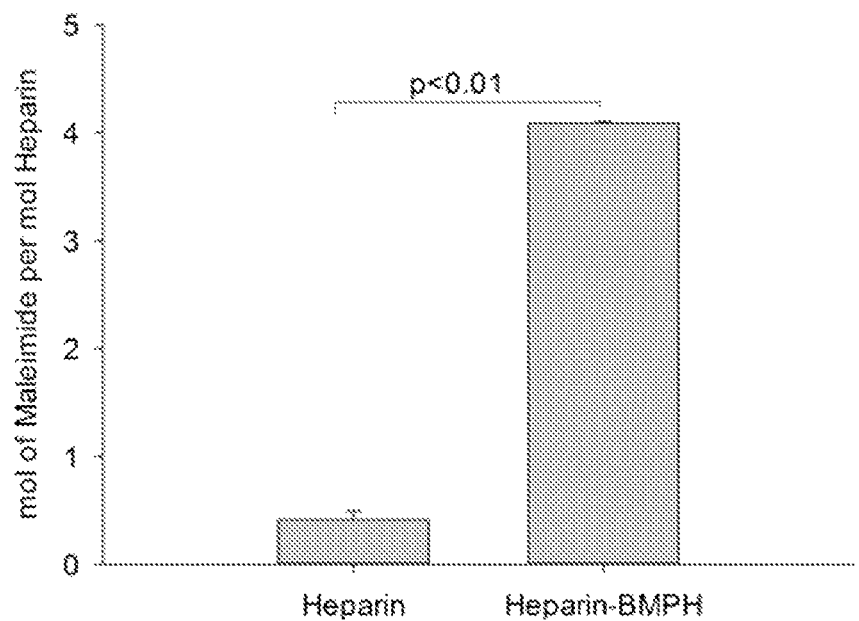
FIGS. 11A-D show graphs depicting the characterization of heparin-BMPH (A, B) and polymer-ECM composites (C, D). (A) Quantification of maleimide group showed significantly higher amount of maleimide groups in heparin-BMPH conjugate compared to heparin control. (B) Factor Xa assay showed anti-factor Xa activity of heparin was not altered with BMPH conjugation bioactivity. (C) Quantification of thiol group showed POC-Cys coating on ECM did not increase free thiol concentration on polymer-ECM composites until reducing reagent BME treatment. (D) Tensile test showed no significant difference in ECM elastic modulus with or without POC-Cys or BME.
Figure 11B:
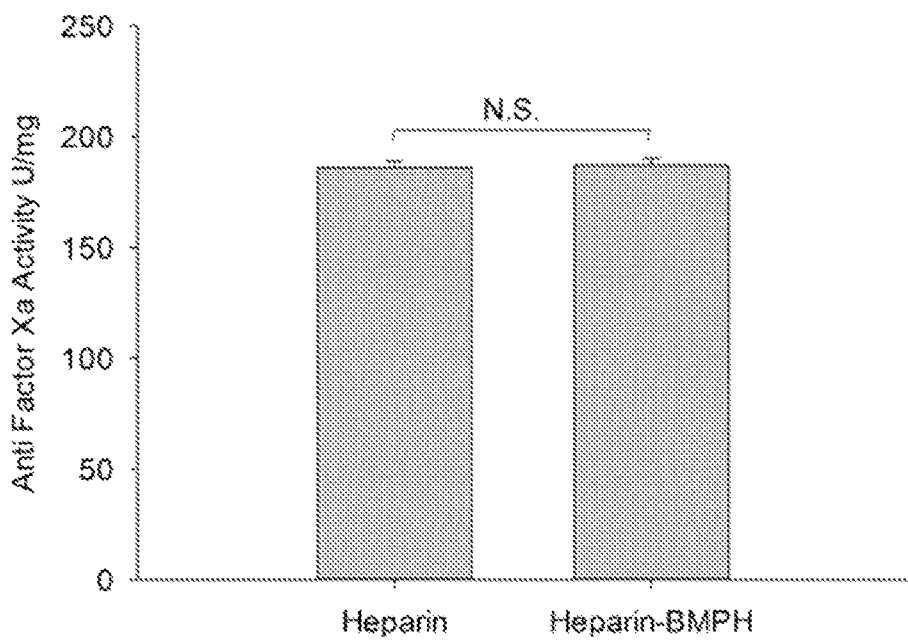

Addition of maleimide group to heparin does not impair heparin bioactivity. The maleimide-containing coupling reagent BMPH was conjugated to heparin at a 10:1 molar ratio during reaction, resulting in a yield of 4.08±0.02 mol of maleimide per mol of heparin (FIG. 11A). Heparin was modified with maleimide functional groups to permit immobilization onto ECM that had been thiolated. Importantly, modification of heparin with BMPH did not alter the anti-coagulant activity of heparin in solution, as per results of its anti-Factor Xa activity (187.3±3.0 U/mg heparin vs. 186.1±1.9 U/mg heparin-BMPH, p=0.639, FIG. 11B). Factor Xa plays a central role in the coagulation cascade, and heparin binds to antithrombin to inactivate factor Xa, providing anticoagulant activity (ref 12; herein incorporated by reference in its entirety).

Figure 11C:
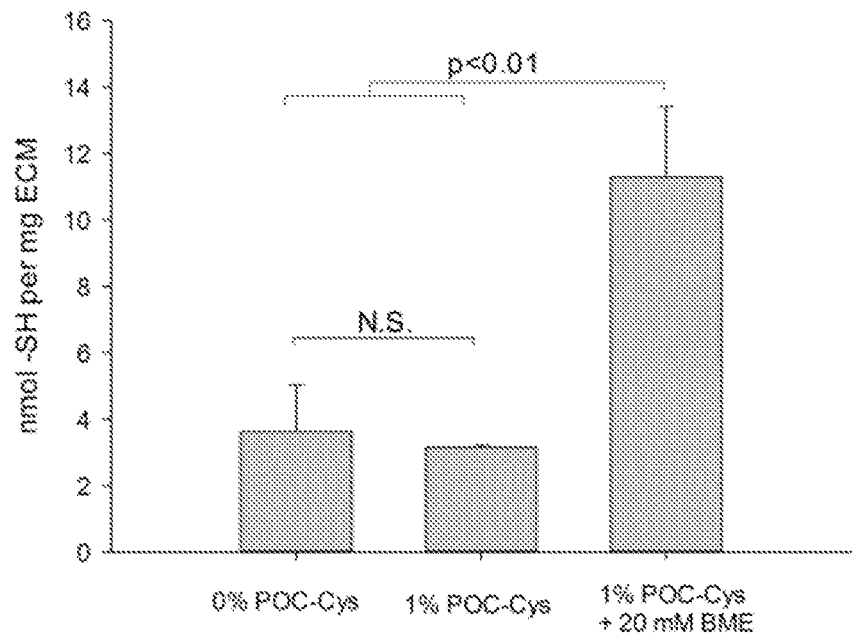

Vascular ECM thiolated via POC-Cys without change in elastic moduli. POC-Cys prepolymer was hybridized onto ECM to form a polymer-ECM composite in order to provide additional thiol groups throughout the ECM, allowing the "click" reaction with maleimide groups of heparin-BMPH to proceed. The polymer-ECM composite was subsequently treated with 2-β Mercaptoethanol (BME) for one hour to break down disulfide bonds and make the thiol groups available. BME treatment resulted in significant increase in thiol concentration (11.28±2.12 nmol/mg after BME treatment vs. 3.15±0.07 nmol/mg before BME treatment, $p<0.01$) (FIG. 11C).

Figure 11D:
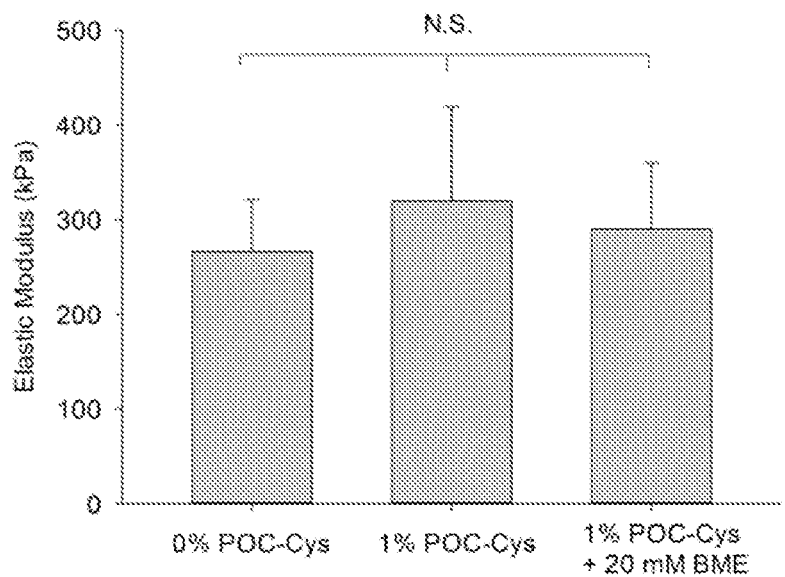

Hybridization of ECM with 1% POC-Cys and subsequent BME treatment did not significantly change ECM mechanical stiffness (elastic modulus for ECM with 0% POC-Cys: 266.5±54.5 kPa; 1% POC-Cys: 319.7±99.7 kPa; and 1% POC-Cys followed by 20 mM BME: 290.0±70.1 kPa, p=0.824) (FIG. 11D), demonstrating that polymer-ECM composites provide additional thiol groups for further modification with maleimide-thiol "click" chemistry for heparinization without altering ECM mechanical property.

In vitro Characterization of Heparinized Polymer-ECM Composites

Figure 12A:
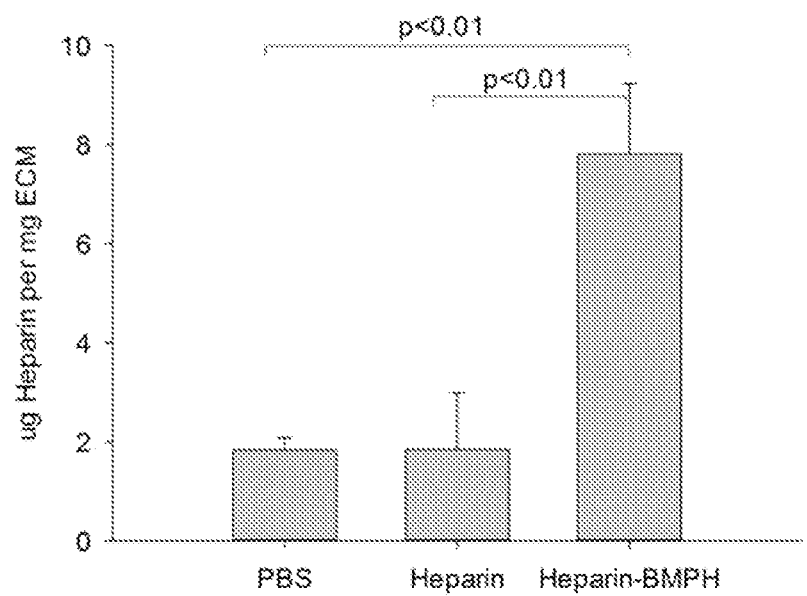
FIGS. 12A-D show graphs depicting the characterization of mechanocompatible polymer-ECM composites after "click" chemistry. (A) Heparin quantification showed significantly higher amount of heparin binding to polymer-ECM composites in the presence of BMPH conjugate, compared to PBS or heparin treated ECM. (B) Platelet adhesion assay showed significantly lower amount of platelet binding to polymer-ECM composites in the presence of BMPH conjugate. (C) Immobilized heparin was stable for 1 week and still partially remained on ECM after 4 weeks of incubation. (D) Heparinized polymer-ECM composites using "click" chemistry did not change ECM elastic modulus compared to native and decellularized artery, as opposed to heparinized cECM using crosslinking chemistry.
Figure 12B:
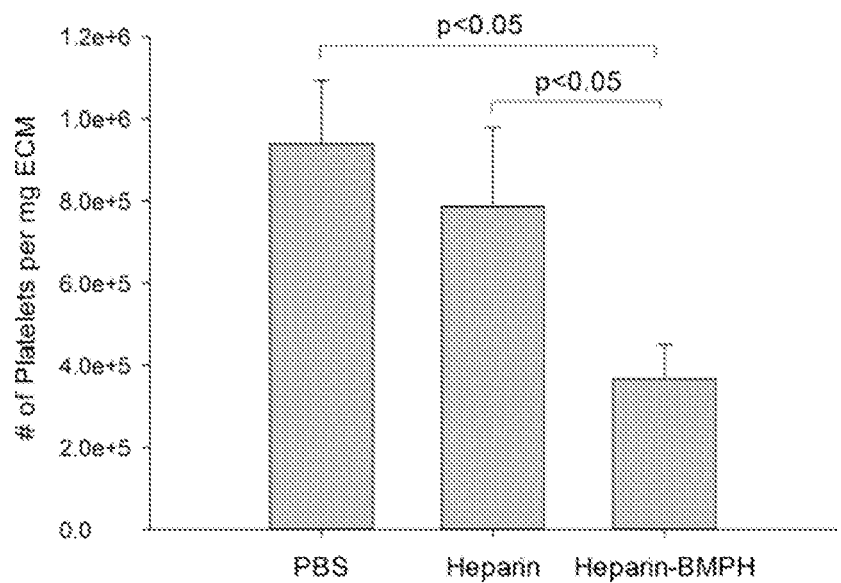
Figure 12C:
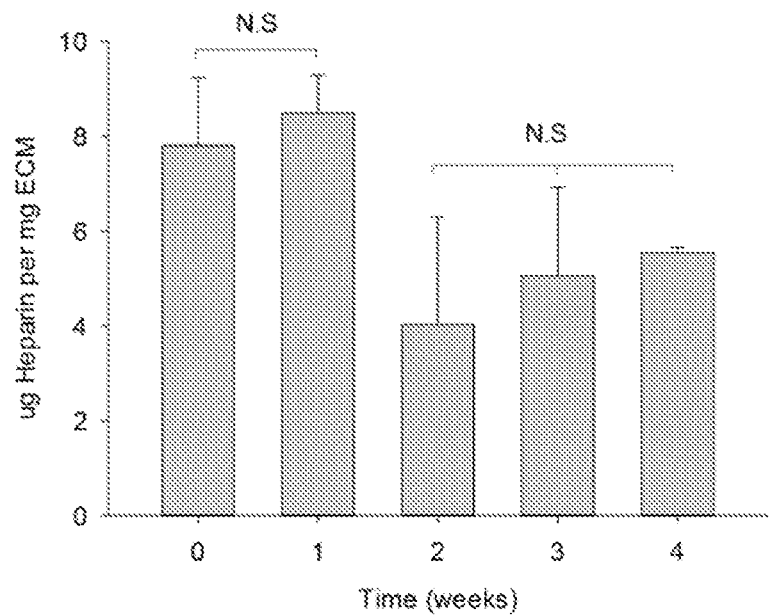

Heparinized polymer-ECM composites are thromboresistant. Glycosaminoglycan (GAG) assay showed significantly higher amount of GAG in heparinized polymer-ECM composites (7.82±1.41 µg/mg ECM) compared to GAGs within decellularized ECM alone (1.83±0.25 µg/mg ECM, $p<0.01$) and non-specific binding between heparin and ECM (1.86±1.14 µg/mg ECM) (FIG. 12A). Platelet activation and adhesion to the ECM is an early initiator of thrombosis and plaque formation (ref 14; herein incorporated by reference in its entirety). Heparinized polymer-ECM composites significantly reduced platelet adhesion by over 60% compared to polymer-ECM treated with PBS or heparin without BMPH, indicating improved thromboresistant property (FIG. 12B). The amount of heparin was stable within the first week with no significant change (7.82±1.41 µg/mg ECM at week 0 vs. 8.50±0.79 µg/mg ECM at week 1), but decreased ~50% after week 1, remaining stable thereafter until the study was terminated at 4 weeks (5.54±1.28 µg/mg ECM at week 4), above the level in untreated ECM (1.83±0.25 µg/mg ECM, $p<0.05$, FIG. 12C). The heparinized polymer-ECM displays similar thromboresistant properties in vitro to heparin immobilized onto polymer-ECM composite by carbodiimide crosslinking chemistry (ref 5; herein incorporated by reference in its entirety).

Figure 12D:
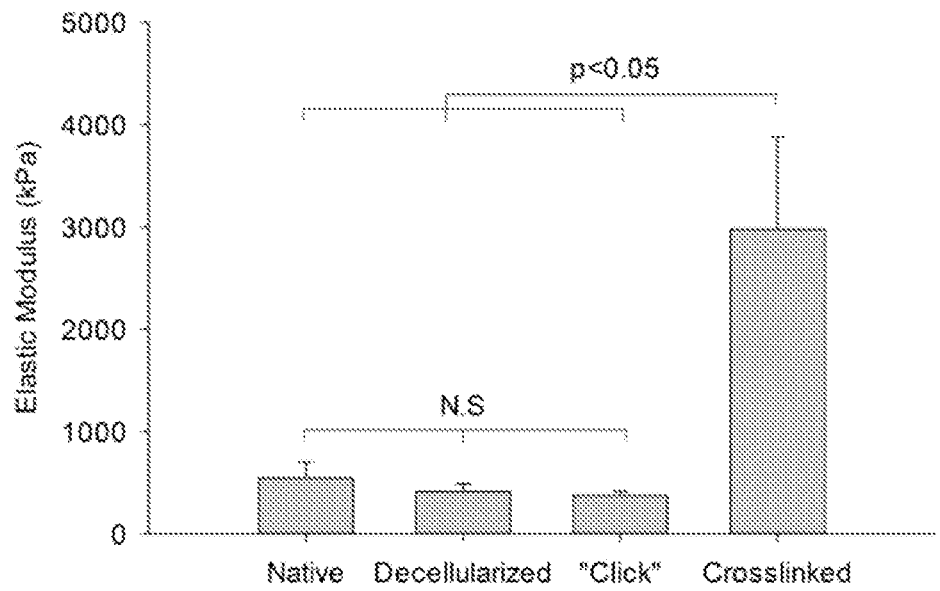

Polymer-ECM composites heparinized via "click" chemistry are mechanocompatible. Despite similar thromboresistance properties, a major difference in the mechanical properties was found between the two heparinized polymer-ECM composites (click vs. crosslinking). Unlike immobilization of heparin via crosslinking, there was no significant change in compliance of the click chemistry modified polymer-ECM composites, compared to native or decellularized rat aorta ECM (FIG. 12D), making it mechanocompatible. Heparinized polymer-ECM composites developed by chemistry that led to ECM crosslinking, on the other hand, revealed significant increase in ECM stiffness, measured by a more than 6-fold increase in elastic modulus (FIG. 12D).

Crosslinking of ECM based biomaterial scaffold is a common practice to enhance their mechanical strength and stabilize the materials against chemical and enzymatic degradation in vivo (ref 15; herein incorporated by reference in its entirety). Various crosslinking agents, such as EDC/NHS (ref 16; herein incorporated by reference in its entirety), glutaraldehyde (ref 17; herein incorporated by reference in its entirety) and genipin (ref 18; herein incorporated by reference in its entirety) have been explored. The degree of crosslinking is difficult to control and results in increased stiffness, cytotoxicity and calcification (ref 15; herein incorporated by reference in its entirety). Moreover, degradation of the ECM scaffold is an essential component that contributes to the overall remodeling events (ref 19; herein incorporated by reference in its entirety). Therefore, it is not necessary to crosslink ECM scaffold to prevent degradation, if the mechanical properties and structural integrity of native tissue are well maintained after decellularization. In experiments conducted during development of embodiments herein, the decellularization process using Triton X-100 and sodium dodecyl sulfate followed with DNAse I treatment retained ECM integrity without significantly weakening material mechanical properties compared to native arteries (FIG. 12D). Therefore, the polymer-ECM composite grafts are mechanocompatible without crosslinking.

In vivo Characterization of Heparinized Polymer-ECM Composites

Figure 14:
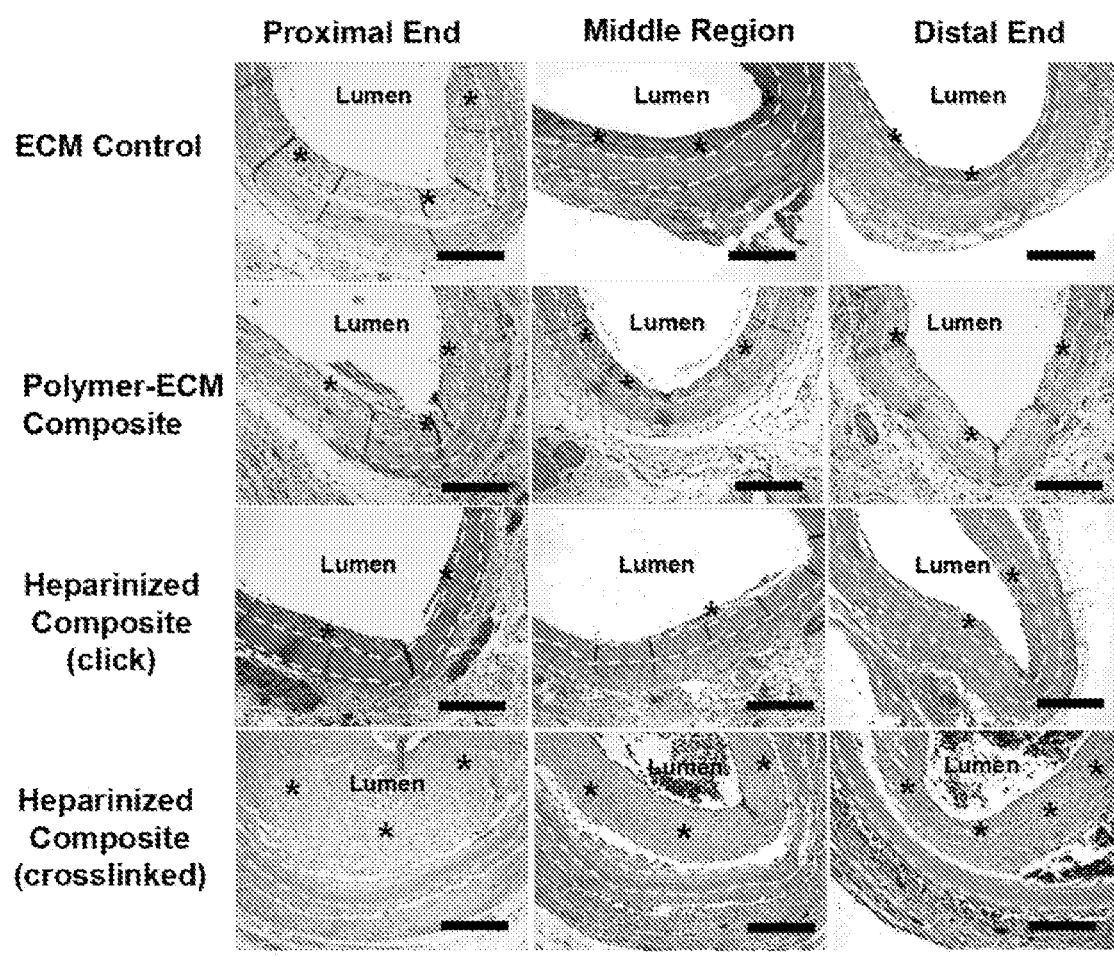
FIG. 14 shows H&E staining for decellularized aorta ECM control, polymer-ECM composite, heparinized polymer-ECM composite (produced via "click" chemistry), and heparinized polymer-cECM composite at proximal end, middle region and distal end. Vascular grafts were harvested from rat aorta interposition model at 4 weeks after implantation and all microscopic images were taken with a 10× objective. Grafts were outlined between yellow dashed lines, while * indicates the presence of intimal hyperplasia. Scale bar=200 μm.
Figure 15:
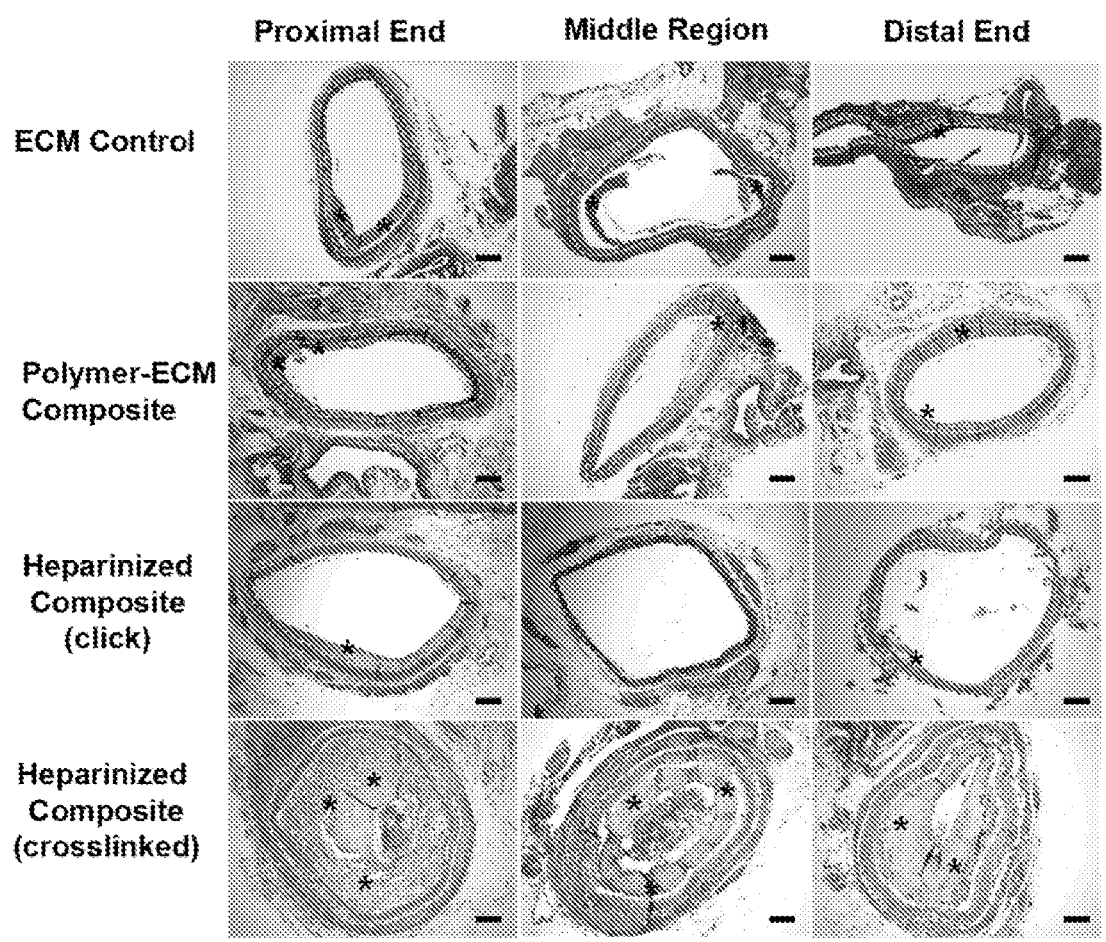
FIG. 15 shows Masson's Trichrome staining for decellularized aorta ECM control, polymer-ECM composite, heparinized polymer-ECM composite via "click" chemistry, and heparinized polymer-cECM composite via crosslinking chemistry at proximal end, middle region and distal end. AVascular grafts were harvested from rat aorta interposition model at 4 weeks after implantation and all microscopic images were taken with a 4× objective. Grafts were outlined between yellow dashed lines, while * indicates the presence of intimal hyperplasia. Scale bar=200 μm.

A rat abdominal aorta interposition model (ref 20; herein incorporated by reference in its entirety) was used to test patency and biocompatibility of ECM based vascular grafts in vivo (FIG. 13A,B). Recipient animals received one or four types of grafts: (1) decellularized donor rat abdominal aortas without any modification (ECM Control); (2) POC modified ECM composites without heparin (Polymer-ECM Composite); (3) heparin modified polymer-ECM composite grafts by "click" chemistry (Heparinized Composite); and (4) heparin modified polymer-ECM composites with crosslinking chemistry (Heparin-crosslinked)). All grafts remained in the subjects during the 4-week time frame, as observed by in vivo Doppler ultrasound imaging technique. All grafts were harvested at 4 weeks after surgery and histology compared segmentally along the length (proximal, middle, and distal) of the graft (FIGS. 14 and 15).

Figure 16:
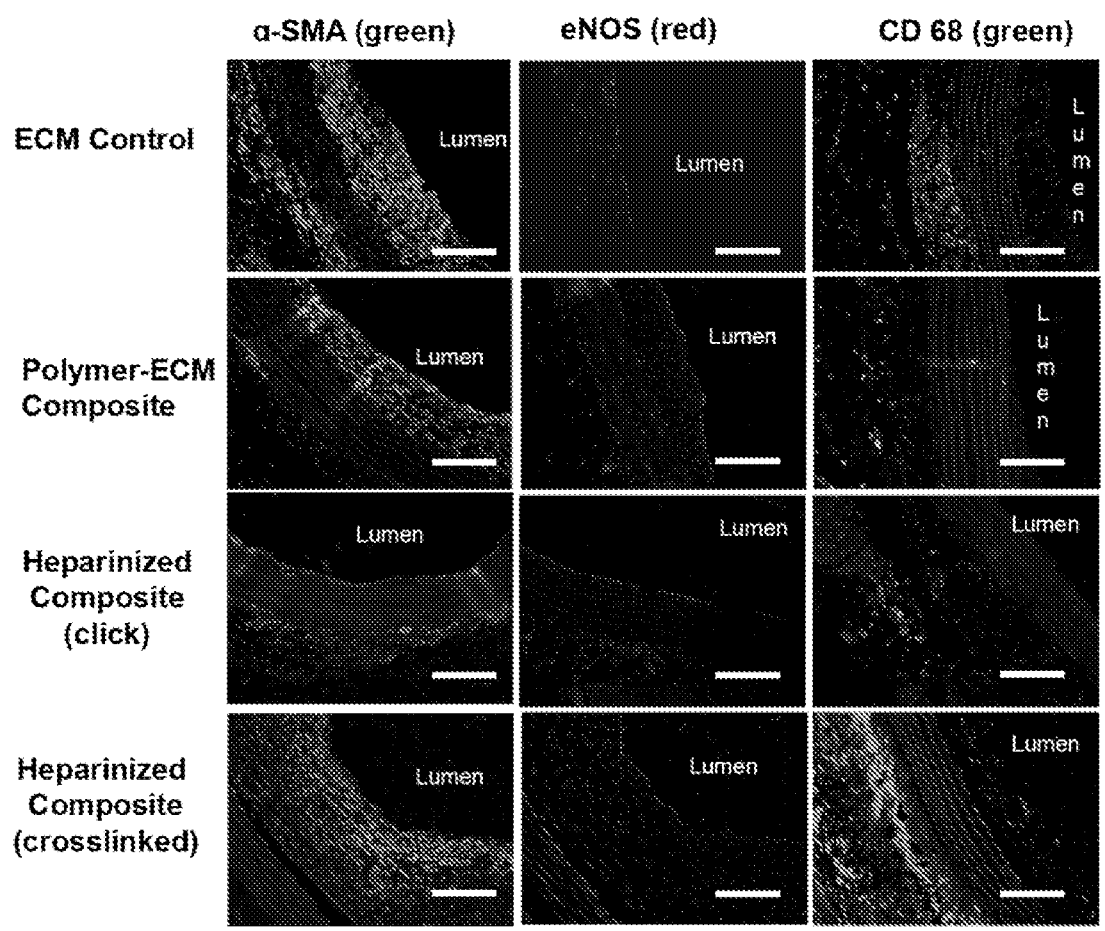
FIG. 16 shows immunofluorescence staining of α-SMA, eNOS, and CD 68 for decellularized aorta ECM control, polymer-ECM composite, heparinized polymer-ECM composite via "click" chemistry, and heparinized polymer-cECM composite via crosslinking chemistry at midgraft. All grafts were harvested from rat aorta interposition model at 4 weeks after implantation. Scale bar=100 μm.
Figures 17A, 17B, 17C:
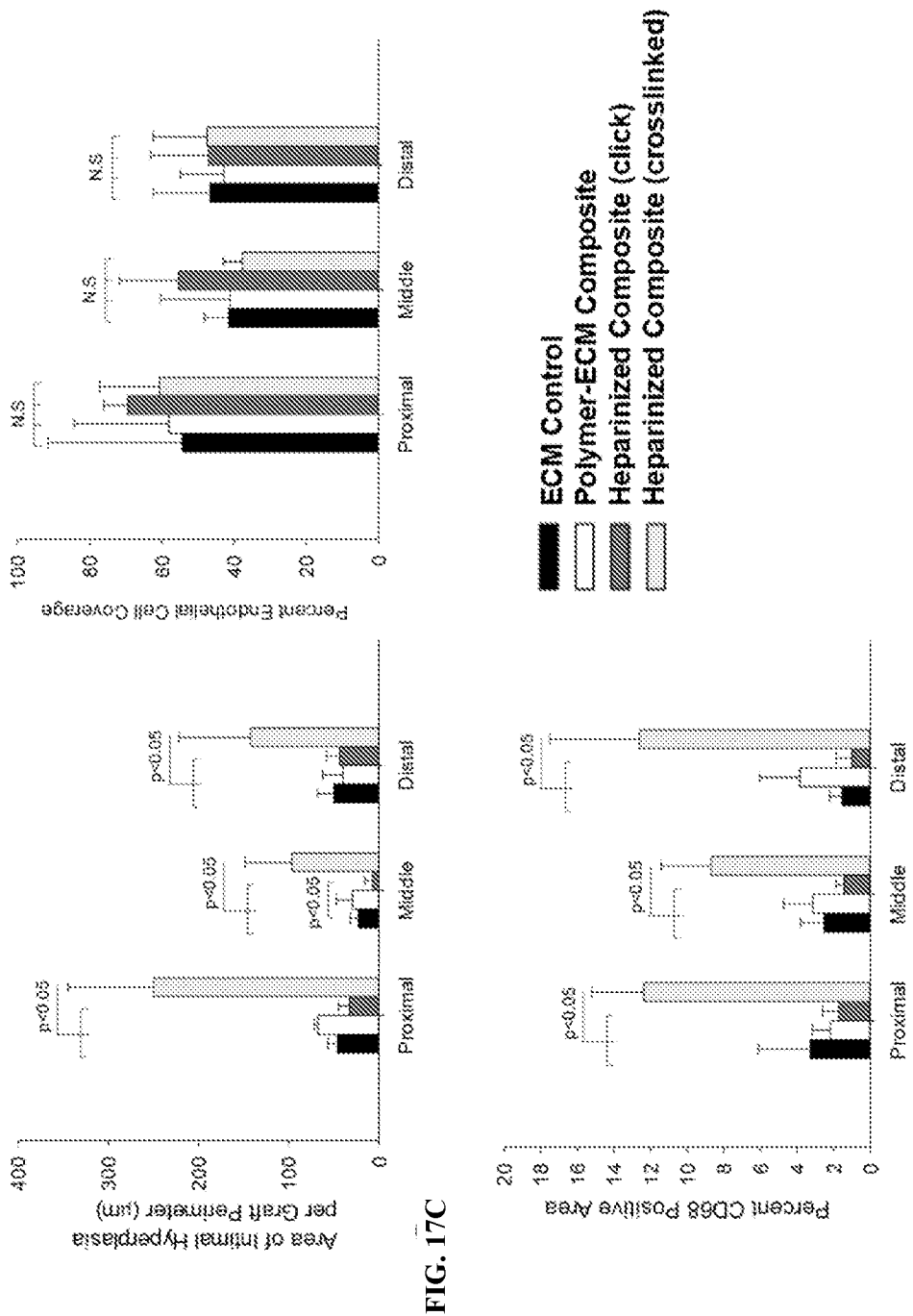
FIGS. 17A-C show graphs depicting quantitative analysis of intimal hyperplasia (A), endothelial cell coverage (B), and macrophage density (C) for decellularized aorta ECM control, polymer-ECM composite, heparinized polymer-ECM composite via "click" chemistry, and heparinized polymer-cECM composite via crosslinking chemistry at proximal end, middle region and distal end.

Mechanocompatible vascular grafts exhibit reduced intimal hyperplasia. Intimal hyperplasia formation within ECM-based vascular grafts was confirmed by immunofluorescence staining for α-SMA (VSMC marker, FIG. 16). A moderate amount of intimal hyperplasia was formed on the luminal side of ECM control (23.1±8.3 µm midgraft) and polymer-ECM composite grafts (29.1±18.0 µm midgraft), with no significant difference (p=0.614) (FIG. 17A). Heparinized polymer-ECM composites (click) resulted in the least amount of intimal hyperplasia (6.7±6.9 µm midgraft, $p<0.05$ compared to ECM control), while heparin-crosslinked polymer-ECM resulted in the highest amount of intimal hyperplasia (96.5±51.4 µm midgraft, $p<0.05$ compared to ECM control).

Intimal hyperplasia is the over-proliferation of vascular smooth muscle cells (VSMCs), which is a common cause for vascular graft failure (ref 21; herein incorporated by reference in its entirety). Mismatch in compliance and elastic properties between vascular grafts and native vessels is considered as an important, if not the primary, contributing factor to intimal hyperplasia formation (refs. 21,22: herein incorporated by reference in their entireties). Compliance mismatch between vascular grafts and native vessels leads to changes in haemodynamic flow, causing turbulence that injures endothelial cells (ref 23; herein incorporated by reference in its entirety), and stimulates VSMCs from a fully differentiated, quiescence phenotype to a highly proliferative, migrating phenotype (ref 24; herein incorporated by reference in its entirety). Therefore, the ideal vascular graft mimics the mechanical properties of native artery as closely as possible (mechanocompatible) to minimize intimal hyperplasia formation and maximize graft patency.

Experiments conducted during development of embodiments herein demonstrated that heparin and cECM led to severe intimal hyperplasia in 4 weeks, contemplated to be related to the increase in stiffness caused by tissue crosslinking, leading to compliance mismatch between the grafts and native vessels. On the other hand, mechanocompatible heparinized (click) composite decreased intimal hyperplasia formation, due to the effect of heparin in inhibiting VSMC proliferation (ref 25; herein incorporated by reference in its entirety) and migration (ref 26; herein incorporated by reference in its entirety), while maintaining ECM mechanical properties compared to native arteries. The dramatic difference between heparinized polymer-ECM composites with or without crosslinking demonstrates the importance of maintaining the mechanocompatibility of vascular grafts.

Polymer-ECM composites support endothelialization. Despite complete decellularization and the lack of a step to reconstitute the cellular components of the grafts prior to implantation, endothelial cells (ECs) were identified along the luminal side of all grafts by staining for eNOS (FIG. 16). Specifically, partial EC coverage was observed for all grafts with no significant difference between groups (FIG. 17B). Since no ECs were pre-seeded to the ECM-based vascular grafts, all ECs present on the lumen were recruited from the recipient animal during the 4 weeks of implantation, either through migration of ECs from the native artery, or via deposition and differentiation of circulating endothelial progenitor cells (EPCs) from blood.

An intact, functional EC lining plays a pivotal role in maintaining vascular function, including selective barrier and filtration, thromboresistance, and inflammation mediation (ref 11; herein incorporated by reference in its entirety). Vascular grafts that were pre-seeded with ECs prior to implantation have shown improved graft patency (ref 28; herein incorporated by reference in its entirety) and decreased intimal hyperplasia formation (ref 29; herein incorporated by reference in its entirety). The mechanocompatible heparinized polymer-ECM composites did not influence in situ endothelialization during our time frame (4 weeks), compared to other groups, resulting in partial EC coverage. EC coverage may improve over time as the EC layer becomes more confluent along the grafts.

Inflammation is reduced in mechanocompatible vascular grafts. Evaluation of macrophages as a surrogate marker of inflammatory response to grafts was assessed via immunofluorescence staining for CD68 (macrophage marker, FIG. 16). CD 68 positive cells were primarily found on the outer layer of each graft, with a higher amount of positive cells found in heparin-crosslinked ECM (8.7±2.7% midgraft) than any other group, including the mechanocompatible heparinized polymer-ECM composite (c1.5±0.4% midgraft, $p<0.01$ compared to crosslinked) (FIG. 17C). In addition, a small number of CD 68 positive cells were also observed within the thick layer of intimal hyperplasia of the crosslinked grafts. This indicates a severe inflammatory response to the crosslinked grafts. Inflammation is associated with an increase in tissue stiffness in numerous pathological conditions, such as cancer (ref 32; herein incorporated by reference in its entirety), liver fibrosis (ref 33; herein incorporated by reference in its entirety), atherosclerosis (ref 34; herein incorporated by reference in its entirety), and osteoarthritis (ref 35; herein incorporated by reference in its entirety), indicating the importance of maintaining mechano-compatibility for ECM based vascular graft and other biomaterial scaffolds, without unnecessary crosslinking that experiments conducted during development of embodiments herein indicate gives rise to undesirable inflammation.

Figure 18:
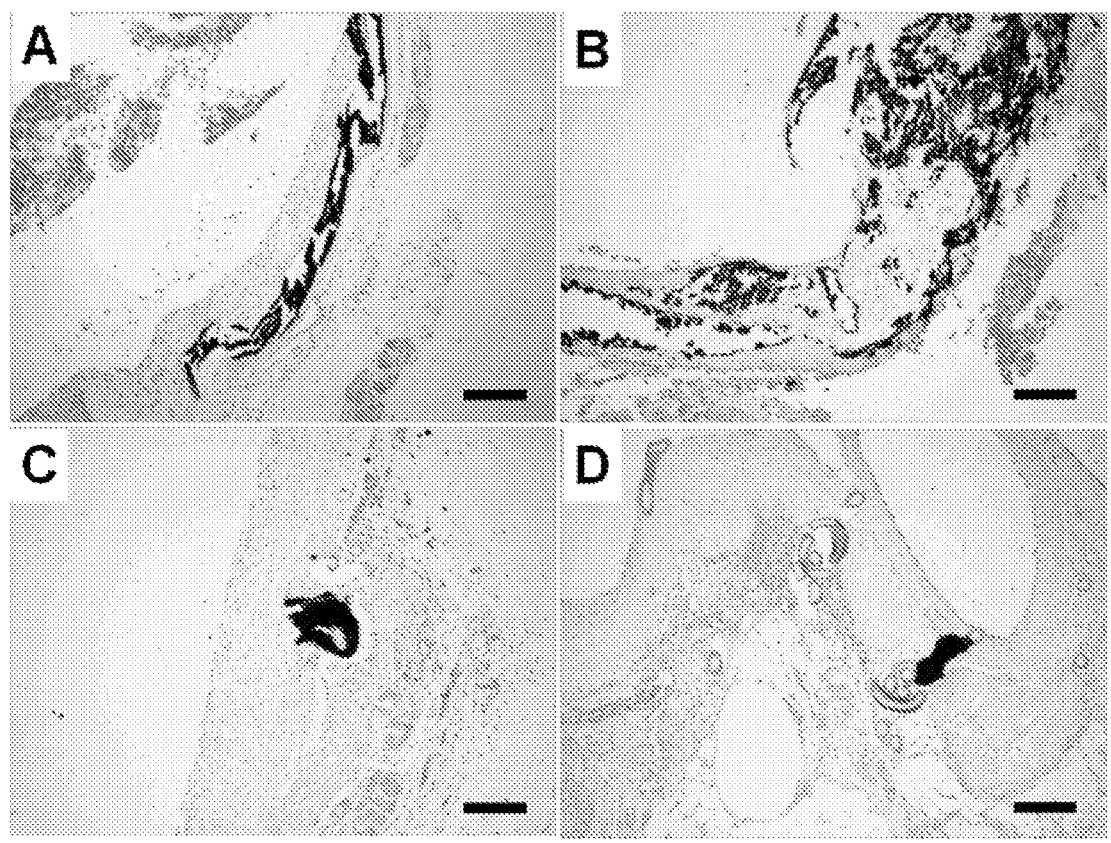
FIG. 18 shows Von Kossa staining for calcification in the vascular wall of (panel A) ECM control graft, (panel B) heparinized polymer-cECM composite (crosslinked) graft, and at the anastomosis site of (panel C) polymer-ECM composite graft, (panel D) heparinized polymer-ECM composite (click) graft. Dark black color indicates calcification in Von Kossa staining, while cell nuclei are visible). Scale bar=100 µm.

Calcification within the vascular graft wall, possibly as a result of inflammation (ref 36; herein incorporated by reference in its entirety), was observed in 25% ECM control grafts (FIG. 18A), and 50% of heparin-crosslinked grafts (Supplemental FIG. 18B). Calcification was not observed within the vascular walls of polymer-ECM composite or heparinized polymer-ECM composite (click) grafts, but was found at the anastomosis adjacent to sutures in 25% of grafts (FIG. 18C, D). Calcification is a known problem for many ECM-based cardiovascular prostheses, including acellular heart valves (ref 37; herein incorporated by reference in its entirety) and vascular grafts (ref 38; herein incorporated by reference in its entirety). A number of molecules are considered inhibitors for vascular calcification, including inorganic pyrophosphate (ref 40; herein incorporated by reference in its entirety), Matrix Gla-protein (MGP) (ref 41; herein incorporated by reference in its entirety) and fetuin (ref 42; herein incorporated by reference in its entirety), which in some embodiments, may be incorporated into the polymer-ECM composites via surface modification and/or sustained release to prevent the process.

REFERENCES

The following references, some of which are referenced above by number, are herein incorporated by reference in their entireties.

[1] M. Albers, V. M. Battistella, M. Romiti, A. A. Rodrigues, C. A. Pereira, Journal of vascular surgery 2003, 37, 1263.

[2] C. Quint, M. Arief, A. Muto, A. Dardik, L. E. Niklason, Journal of vascular surgery 2012, 55, 790.

[3] H. Bergmeister, R. Plasenzotti, I. Walter, C. Plass, F. Bastian, E. Rieder, W. Sipos, A. Kaider, U. Losert, G. Weigel, Journal of Biomedical Materials Research Part B: Applied Biomaterials 2008, 87B, 95.

[4] S. L. Dahl, J. Koh, V. Prabhakar, L. E. Niklason, Cell transplantation 2003, 12, 659; S. L. Dahl, A. P. Kypson, J. H. Lawson, J. L. Blum, J. T. Strader, Y. Li, R. J. Manson, W. E. Tente, L. DiBernardo, M. T. Hensley, Science translational medicine 2011, 3, 68ra9.

[5] B. Jiang, B. Akgun, R. C. Lam, G. A. Ameer, J. A. Wertheim, Acta biomaterialia 2015, 18, 50.

[6] S. Murugesan, J. Xie, R. J. Linhardt, Current topics in medicinal chemistry 2008, 8, 80.

[7] B. Conklin, E. Richter, K. Kreutziger, D.-S. Zhong, C. Chen, Medical engineering & physics 2002, 24, 173; M. Zhou, Z. Liu, Z. Wei, C. Liu, T. Qiao, F. Ran, Y. Bai, X. Jiang, Y. Ding, Artificial organs 2009, 33, 230.

[8] S. F. Badylak, D. O. Freytes, T. W. Gilbert, Acta Biomaterialia 2009, 5, 1.

[9] J. Yang, D. Motlagh, J. B. Allen, A. R. Webb, M. R. Kibbe, O. Aalami, M. Kapadia, T. J. Carroll, G. A. Ameer, Advanced Materials 2006, 18, 1493.

[10] R. van Lith, E. K. Gregory, J. Yang, M. R. Kibbe, G. A. Ameer, Biomaterials 2014, 35, 8113.

[11] B. Jiang, L. Perrin, D. Kats, T. Meade, G. Ameer, Biomaterials 2015, 69, 110.

[12] E. W. Davie, Journal of Biological Chemistry 2003, 278, 50819; J. Hirsh, R. Raschke, CHEST Journal 2004, 126, 188S.

[13] J. Yang, Y. Zhang, S. Gautam, L. Liu, J. Dey, W. Chen, R. P. Mason, C. A. Serrano, K. A. Schug, L. Tang, Proceedings of the National Academy of Sciences 2009, 106, 10086.

[14] W. Bergmeier, C. L. Piffath, T. Goerge, S. M. Cifuni, Z. M. Ruggeri, J. Ware, D. D. Wagner, Proceedings of the National Academy of Sciences 2006, 103, 16900.

[15] C. E. Schmidt, J. M. Baier, Biomaterials 2000, 21, 2215.

[16] S.-N. Park, J.-C. Park, H. O. Kim, M. J. Song, H. Suh, Biomaterials 2002, 23, 1205.

[17] S. P. Pilipchuk, M. K. Vaicik, J. C. Larson, E. Gazyakan, M. H. Cheng, E. M. Brey, Journal of Biomedical Materials Research Part A 2013, 101, 2883.
[18] Y. Chang, C.-C. Tsai, H.-C. Liang, H.-W. Sung, Biomaterials 2002, 23, 2447.
[19] S. F. Badylak, T. W. Gilbert, Seminars in Immunology 2008, 20, 109.
[20] G. H. Borschel, Y.-C. Huang, S. Calve, E. M. Arruda, J. B. Lynch, D. E. Dow, W. M. Kuzon, R. G. Dennis, D. L. Brown, Tissue engineering 2005, 11, 778.
[21] M. S. Lemson, J. H. M. Tordoir, M. J. A. P. Daemen, P. J. E. H. M. Kitslaar, European Journal of Vascular and Endovascular Surgery 2000, 19, 336.
[22] P. D. Ballyk, C. Walsh, J. Butany, M. Ojha, Journal of Biomechanics 1997, 31, 229; S. Greenwald, C. Berry, The Journal of pathology 2000, 190, 292; S. Sarkar, H. Salacinski, G. Hamilton, A. Seifalian, European journal of vascular and endovascular surgery 2006, 31, 627.
[23] H. Haruguchi, S. Teraoka, J Artif Organs 2003, 6, 227.
[24] A. C. Newby, A. B. Zaltsman, The Journal of Pathology 2000, 190, 300.
[25] J. Castellot, L. Favreau, M. Karnovsky, R. Rosenberg, Journal of Biological Chemistry 1982, 257, 11256.
[26] R. A. Majack, A. W. Clowes, Journal of cellular physiology 1984, 118, 253.
[27] K. Shimizu, S. Sugiyama, M. Aikawa, Y. Fukumoto, E. Rabkin, P. Libby, R. N. Mitchell, Nature medicine 2001, 7, 738.
[28] S. Kaushal, G. E. Amiel, K. J. Guleserian, O. M. Shapira, T. Perry, F. W. Sutherland, E. Rabkin, A. M. Moran, F. J. Schoen, A. Atala, Nature medicine 2001, 7, 1035.
[29] D. P. Griese, A. Ehsan, L. G. Melo, D. Kong, L. Zhang, M. J. Mann, R. E. Pratt, R. C. Mulligan, V. J. Dzau, Circulation 2003, 108, 2710.
[30] W. T. Wong, N. F. Huang, C. M. Botham, N. Sayed, J. P. Cooke, Circulation research 2012, 111, 1363.
[31] A. J. Melchiorri, N. Hibino, J. P. Fisher, Tissue Engineering Part B: Reviews 2013, 19, 292.
[32] J. P. Iredale, Journal of Clinical Investigation 2007, 117, 539.
[33] K. R. Levental, H. Yu, L. Kass, J. N. Lakins, M. Egeblad, J. T. Erler, S. F. Fong, K. Csiszar, A. Giaccia, W. Weninger, Cell 2009, 139, 891.
[34] S. Park, E. G. Lakatta, Yonsei medical journal 2012, 53, 258.
[35] M. Maldonado, J. Nam, BioMed research international 2013, 2013.
[36] J.-S. Shao, S.-L. Cheng, J. Sadhu, D. A. Towler, Hypertension 2010, 55, 579.
[37] M. T. Bailey, S. Pillarisetti, H. Xiao, N. R. Vyavahare, Journal of Biomedical Materials Research Part A 2003, 66, 93; G. Steinhoff, U. Stock, N. Karim, H. Mertsching, A. Timke, R. R. Meliss, K. Pethig, A. Haverich, A. Bader, Circulation 2000, 102, Iii.
[38] A. Assmann, P. Akhyari, C. Delfs, U. Flogel, C. Jacoby, H. Kamiya, A. Lichtenberg, Journal of Surgical Research 2012, 176, 367.
[39] R. C. Johnson, J. A. Leopold, J. Loscalzo, Circulation research 2006, 99, 1044.
[40] H. Fleisch, D. Schibler, J. Maerki, I. Frossard, 1965.
[41] L. J. Schurgers, E. C. Cranenburg, C. Vermeer, Thromb Haemost 2008, 100, 593.
[42] J. L. Reynolds, J. N. Skepper, R. McNair, T. Kasama, K. Gupta, P. L. Weissberg, W. Jahnen-Dechent, C. M. Shanahan, Journal of the American Society of Nephrology 2005, 16, 2920.
[43] G. L. Ellman, K. D. Courtney, V. Andres, R. M. Featherstone, Biochemical pharmacology 1961, 7, 88.
[44] R. W. Farndale, C. A. Sayers, A. J. Barrett, Connective tissue research 1982, 9, 247.
[45] E. Pektok, B. Nottelet, J.-C. Tille, R. Gurny, A. Kalangos, M. Moeller, B. H. Walpoth, Circulation 2008, 118, 2563.

The invention claimed is:

1. A composition comprising a composite of:
    (a) extracellular matrix (ECM), and
    (b) a polymer of citric acid, aliphatic diol, and cysteine monomers covalently linked to a bioactive agent.

2. The composition of claim 1, wherein the composite is a homogeneous composite.

3. The composition of claim 1, wherein the ECM is decellularized ECM.

4. The composition of claim 1, wherein the ECM is not crosslinked substantially more than naturally-occurring ECM in vivo.

5. The composition of claim 1, wherein the aliphatic diol monomers are 4-16 carbons in length with terminal OH groups.

6. The composition of claim 5, wherein the aliphatic diol monomers comprise 1,8-octandiol.

7. The composition of claim 1, wherein the bioactive agent is selected from an anticoagulant, growth factor, cytokine, and hormone.

8. A method of immobilizing a bioactive agent within ECM comprising:
    (a) generating or obtaining a composition of claim 1;
    (b) reacting a thiol-reactive group on the bioactive agent with a free thiol on the polymer, thereby immobilizing the bioactive agent on the polymer and within the ECM.

9. The method of claim 8, further comprising a prior step of reacting the bioactive agent with a molecular entity comprising the thiol-reactive group.

10. The method of claim 8, wherein generating the composition of claim 1 comprisies contacting the ECM with a pre-polymer of citric acid, aliphatic diol, and cysteine monomers and allowing the pre-polymer to further polymerize within the ECM to form the composite.

11. The method of claim 10, further comprising (i) combining the citric acid, aliphatic diol, and cysteine monomers and polymerizing the monomers to form the pre-polymer.

12. The method of claim 8, wherein the ECM is decellularized ECM.

13. The method of claim 8, wherein the ECM is not crosslinked substantially more than naturally-occurring ECM in vivo.

14. The method of claim 8, wherein the aliphatic diol monomers comprise 1,8-octandiol.

15. The method of claim 8, wherein the bioactive agent is selected from an anticoagulant, growth factor, cytokine, and hormone.

16. The method of claim 15, wherein the bioactive agent is heparin.

17. A method of tissue repair or engineering, comprising implanting a composition of claim 1 into a subject.

18. A composition comprising a composite of:
    (a) extracellular matrix (ECM), and
    (b) a polymer of citric acid, aliphatic diol, and cysteine monomers covalently linked to a bioactive agent;
wherein the bioactive agent is covalently linked to the polymer at one or more of the cysteine monomers.

19. The composition of claim 18, wherein the polymer is covalently linked to the bioactive agent via a thiolate linkage at the one or more cysteine monomers.

20. A composition comprising a composite of:
(a) extracellular matrix (ECM), and
(b) a polymer of citric acid, aliphatic diol, and cysteine monomers covalently linked to heparin.

* * * * *